(12) United States Patent
Roddiger et al.

(10) Patent No.: US 7,659,074 B2
(45) Date of Patent: *Feb. 9, 2010

(54) DIAGNOSIS AND TREATMENT OF DISORDERS OF IRON METABOLISM

(75) Inventors: Ralf Roddiger, Gorxheimertal (DE); Paul Lehmann, Worms (DE); Lothar Thomas, Frankfurt (DE)

(73) Assignee: Roche Diagnostics Corporation, Indianapolis, IN (US)

( * ) Notice: Subject to any disclaimer, the term of this patent is extended or adjusted under 35 U.S.C. 154(b) by 347 days.

This patent is subject to a terminal disclaimer.

(21) Appl. No.: 10/449,633

(22) Filed: May 30, 2003

(65) Prior Publication Data

US 2003/0232393 A1 Dec. 18, 2003

Related U.S. Application Data

(63) Continuation-in-part of application No. 10/242,061, filed on Sep. 12, 2002, now Pat. No. 7,601,684.

(60) Provisional application No. 60/322,526, filed on Sep. 14, 2001.

(51) Int. Cl.
*G01N 33/48* (2006.01)
*G01N 33/49* (2006.01)
*G01N 33/50* (2006.01)
*G01N 33/555* (2006.01)
*G01N 33/72* (2006.01)

(52) U.S. Cl. ............................... 435/7.1; 436/66; 436/68

(58) Field of Classification Search ........................ None
See application file for complete search history.

(56) References Cited

OTHER PUBLICATIONS

Feelders et al. Regulation of iron metabolism in the acute phase response:IFNg and TNFa induce hypoferraemia, ferritin production and a decrease in circulating transferrin receptors in can European Journal of Clinical Investigation vol. 28, 520-527 (1998).*
Suominen et al. Single values of serum transferrin receptor and transferrin receptor ferritin index can be used to detect true and functional iron deficiency in rheumatoid arthritis . . . Arthritis & Rheumatism, vol. 43, No. 5 pp. 1016-1020 (May 2000).*
Lehmann, et al. S-transferrin-receptor, ferritin and CRP as markers in differential diagnosis of anemias of chronic inflammatory processes. (Abstract, Clinical Chemistry and Laboratory Medicine, vol. 47, No. 6 Supplement, Jul. 2001).*
Looker et al., Increased serum transferrin saturatation is associated with lower serum transferrin receptor concentration. Clinical Chemistry 45:12 pp. 2191-2199 (1999).*
Fishbane et al., Reticulocyte hemoglobin content in the evaluation of iron status of hemodialysis patients. Kidney International 52:217-222 (1997).*
Bovy, et al., *Factors determining the percentage of hypochromic red blood cells in hemodialysis patients*, Kidney International, vol. 56, pp. 1113-1119 (1999).
Tessitore, et al., *The role of iron status markers in predicting response to intravenous iron in haemodialysis patients on maintenance erythropoietin*, Nephrology Dialysis Transplantion, vol. 16, pp. 1416-1423 (2001).
Thomas, et al., *Biochemical Markers and Hematologic Indices in the Diagnosis of Functional Iron Deficiency*, Clinical Chemistry, vol. 48, pp. 1066-1076 (2002).
Hasegawa, Midori, et al., Evaluation of reticulocyte hemoglobin content, percentage of hypochromic red blood cells, and ratio of serum transferring receptor level/serum iron level as markers of iron-deficiency erythropoiesis in patients undergoing hemodialysis, NLM Database accession No. NLM12216478 XP002247472 abstract of Nippon Jinzo Gakkai Shi, Japan 2002, vol. 44, No. 5, pp. 453-463, ISSN: 0385-2385.
Little, David R., *Hemochromatosis: Diagnosis and Management*, American Family Physician, 53:2623-2628 (1996).
Remacha, A., et al., *The role of serum transferring receptor in the diagnosis of iron deficiency*, Haematologica, 83:963-966 (1998).
Beguin, Y., et al., *Acute functional iron deficiency in obese subjects during a very-low energy all-protein diet*, American Journal of Clinical Nutrition, 66:75-79 (1997).

* cited by examiner

*Primary Examiner*—Marianne P Allen
*Assistant Examiner*—Regina M DeBerry
(74) *Attorney, Agent, or Firm*—McDonnell Boehnen Hulbert & Berghoff, LLP

(57) ABSTRACT

The invention concerns a method for detecting disorders of iron metabolism and in particular the differential diagnosis of disorders of iron metabolism by means of three independent parameters. The differential diagnosis can be used to classify disorders of iron metabolism and to recommend the required treatment and to monitor the progress and response to treatment.

3 Claims, 14 Drawing Sheets

| Quadrant | Disorders of iron metabolism | sTfR/log ferritin | CRP concentration | Therapy |
|---|---|---|---|---|
| A: | disorders of iron distribution (potential) | < 3.7 (women) < 3.4 (men) | > 5 mg/l | dependency on the reticulocyte count: erythropoietin dose |
| B: | iron overloading | < 0.9 (women + men) | < 5 mg/l | blood letting |
| C: | normal iron status | 0.9 – 3.7 (women) 0.9 – 3.4 (men) | < 5 mg/l | |
| D: | iron deficiency | > 3.7 (women) > 3.4 (men) | <> 5 mg/l | iron substitution |

FIGURE 2

DIAGNOSIS AND TREATMENT OF DISORDERS OF IRON METABOLISM

CROSS-REFERENCE TO RELATED APPLICATIONS

This application is a continuation in part of application Ser. No. 10/242,061, filed Sep. 12, 2002, now U.S. Pat. No. 7,601,684 which claims the benefit of U.S. Provisional Patent Application No. 60/322,526, filed Sep. 14, 2001.

FIELD OF THE INVENTION

The invention concerns a method for detecting disorders of iron metabolism and in particular the differential diagnosis of disorders of iron metabolism by means of three independent parameters. The differential diagnosis can be used to classify disorders of iron metabolism and to recommend the required treatment and to monitor the progress and response to treatment.

BACKGROUND OF THE INVENTION

Iron as a component of haemoglobin and the cell haemins is one of the most important biocatalysts in the human organism. Disorders of iron metabolism and in particular iron deficiency and perturbations of iron distribution and utilization in chronic general illnesses are among the most frequently overlooked or misinterpreted diseases. One of the main reasons for this is that the determination of transport iron in the serum or plasma which is used in conventional diagnostics does not allow a representative estimation of the total body iron stores due to short-term variations.

The ability to precisely determine the iron storage protein ferritin in plasma provided a method for determining the total body iron stores and thus allowed a more rapid and reliable diagnosis especially of iron deficiency states. Ferritin is an indicator of the amount of storage iron. The soluble transferrin receptor (sTfR) indicates the iron requirements of the cell and erythropoiesis activity. The sTfR/log ferritin index is a measure of the depletion of the iron stores and of the functional iron compartments. In chronic inflammatory diseases such as in infections and especially tumour diseases, iron is redistributed with a relative overload of the iron stores accompanied by a relative deficiency of iron supply to the erythropoietic cells.

Due to the very limited capacity to absorb iron, the iron requirements can only be met by recycling functional iron. It is stored in the form of ferritin and haemosiderin. Each cell is able to take up a surfeit of iron by synthesizing ferritin and the basic mechanisms for this are identical in all types of cells. The transferrin-iron$^{3+}$ complex is bound to the transferrin receptor of the cell membrane. The uptake of iron can be regulated by the transferrin receptor expression. In addition iron induces the synthesis of apoferritin. Hence in the majority of metabolic situations a representative proportion of the synthesized ferritin is released into the blood plasma.

However, even if the above-mentioned parameters are employed, it is not in practice possible or very difficult to routinely determine and differentiate between various iron states.

Therefore an object of the present invention was to provide a method which enables the reliable detection of disorders of iron metabolism in a simple manner.

SUMMARY OF THE INVENTION

This object is achieved according to the invention by a method for determining the iron status and in particular for detecting disorders of iron metabolism comprising the determination of:

(i) a parameter which allows a determination of the total body iron stores, (ii) a parameter which allows a determination of the erythropoietic maturation process and/or its activity and (iii) a parameter which allows a determination of unspecific disorders of iron metabolism.

Hence the invention concerns the differential diagnosis of disorders of iron metabolism by means of three independent parameters.

The determination of the total body iron stores can for example be carried out by measuring the parameters erythrocyte ferritin, zinc protoporphyrin, haemoglobin, myoglobin, transferrin and transferrin saturation, ferritin, haemosiderin or/and the enzymes catalase, peroxidase or/and cytochrome. A determination of the concentration or activities of these parameters enables a determination of the total body iron stores which is determined as parameter (i) of the method according to the invention. Ferritin or transferrin and particularly preferably ferritin is used as the parameter.

The erythropoietic maturation process and/or the erythropoietic activity can for example be ascertained or determined using erythrocyte indices, reticulocyte indices, FS-e (forward scatter erythrocytes) and/or the soluble transferrin receptor (sTfR). The amount or concentration of soluble transferrin receptor (sTfR) is particularly preferably determined as parameter (ii) in the method according to the invention and used as a parameter for the erythropoietic maturation process or its activity.

Biochemical parameters as well as haematological parameters can be used as a parameter for determining unspecific disorders of iron metabolism. Acute phase proteins and regulators of acute phase protein synthesis are preferably used as biochemical parameters whereas disorders of reticulocyte synthesis are preferably used as haematological parameters. Examples of acute phase proteins whose amount or concentration is determined in order to determine unspecific disorders of iron metabolism comprise C-reactive protein (CRP), serum amyloid A (SAA), $\alpha_1$-anti-chymotrypsin, acidic $\alpha_1$-glycoprotein, $\alpha_1$-antitrypsin, haptoglobin, fibrinogen, complement component C3, complement component C4 or/and coeruloplasmin. Examples of regulators of acute phase protein synthesis are interleukin 6 (IL-6), leukaemia inhibiting factor (LIF), oncostatin M, interleukin 11 (IL-11), ciliary neurotropic factor (CNTF), interleukin 1α (IL-1α), interleukin 1β (IL-1β), tumour necrosis factor-α (TNFα), tumour necrosis factor-β (TNFβ), insulin, fibroblast growth factor (FGF), hepatocyte growth factor, transgrowth factor β (TGFβ) or/and interferon.

Disorders of reticulocyte synthesis such as $CH_2$, reticulocyte count, Hb content of reticulocytes (CHr), IRF (immature reticulocyte fraction) new RBC and reticulocyte fluorescence parameters and/or FS-r (forward scatter reticulocytes) are haematological parameters that can be used in particular as parameter (iii) of the method according to the invention. CRP, SAA or/and CHr are preferred.

BRIEF DESCRIPTION OF THE FIGURES

FIG. 2 shows an example of an input for an anaemia program, the classification of the four quadrants A, B, C, D in a diagram of CRP against sTfR/log ferritin, the classification of the squares and the treatment recommended in each case.

DETAILED DESCRIPTION

Figure 1:
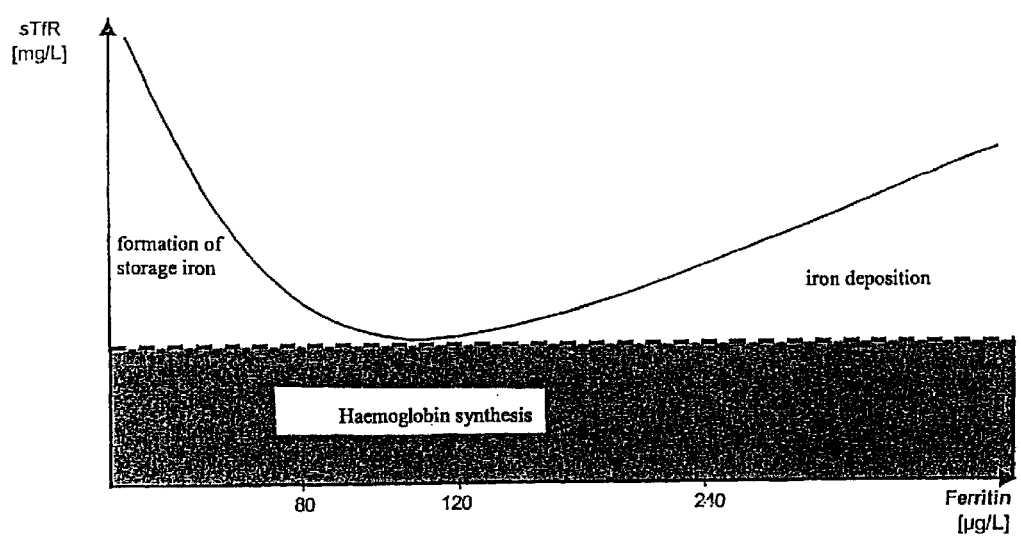
FIG. 1 shows that the soluble transferrin receptor (sTfR) is a parameter for three types of iron status. For (A) (iron distribution disturbance) this means Hb synthesis plus iron deposition, for (B) (iron overloading) Hb synthesis plus iron deposition, for (C) (normal iron status) Hb synthesis and for (D) (iron deficiency) Hb synthesis plus storage iron.

According to the invention it was surprisingly found that rapid and reliable information on the iron status of patients can be obtained by combining three independent parameters. In particular it was found that biochemical or haematological markers and in particular inflammatory markers which are unspecific as such, can be used in an appropriate combination with other parameters to determine the iron status.

In particular the method according to the invention allows a classification of the iron status and in particular of disorders of iron metabolism.

The combination of three independent parameters enables a routine differentiation between normal iron status, iron deficiency, iron distribution disorders and/or iron overloading. In particular the method according to the invention allows a differentiation between normal iron status and iron overloading. In addition it allows a differentiation between the status of iron deficiency and iron distribution disorders. Perturbations of iron distribution can lead to chronic diseases such as rheumatism, asthma or tumours and hence an early detection of iron distribution disorders is of particular importance.

In a particularly preferred embodiment the iron status determined by the method according to the invention is classified in one of the following groups:
(A) iron distribution disorder or/and iron utilization disorder with acute phase reaction,
(B) iron overloading,
(C) normal iron status, and
(D) deficiency of storage iron.

The evaluation of the determined parameters can be preferably assisted by a computer for example by use of an anaemia program. Furthermore the determined measurements are preferably represented graphically in the form of diagrams in order to easily assign the measuring ranges to the various iron states. For example parameter (iii) can be plotted on the ordinate and the ratio of parameter (ii) to parameter (i) can be plotted on the abscissa. This results in various measuring ranges (fields in the diagram) for the various iron states and iron overloading can be distinguished from a normal iron status, and a normal iron status can be distinguished from iron deficiency and also from iron distribution disturbances such as tumour anaemia, chronic anaemia, rheumatoid arthritis or renal anaemia.

The method according to the invention can also be used to specify in a simple manner the treatment required for the respective patient depending on the determined iron status. Thus for example erythropoietin (EPO) therapy is indicated for a classification in group (A), blood letting is indicated for a classification in group (B), no therapy is indicated for a classification in group (C) and iron substitution is indicated when classified in group (D). These therapeutic recommendations are based on the fact that erythropoiesis is mainly regulated by the growth factor EPO and by iron, and the various types of iron metabolism disorders require different treatments that can be determined by the method according to the invention. An iron deficiency leads in particular to a deficit in haemoglobin formation, to hypochromic mycrocytes/anulocytes and thus to anaemias which are manifested as iron deficiency and chronic bleeding. Deficiency of erythropoietin (EPO) results in a reduced proliferation and thus to anaemias that manifest themselves as iron distribution disturbances, acute phase conditions, infections, chronic inflammation, tumour anaemias and renal anaemias.

In addition to the treatment of disorders of iron metabolism, the method according to the invention also allows observation or/and monitoring of the progress and response to treatment and thus ensures an optimal use of EPO or iron preparations (e.g. oral or parenteral iron preparations) in individual patients.

Depending on the selected characteristic values of the above mentioned parameters, the method according to the invention also allows a sex-specific discrimination or differentiation of the individual iron status in which the normal values or cut-off values can then be established for each sex (male or female).

Surprisingly, it was found that chronic diseases, even in very early stages, result in a classification in group (A). Thus, chronic diseases such as chronic renal diseases and chronic inflammatory diseases can be diagnosed with the method according to the invention. In particular, diseases such as renal insufficiency, malignancies, rheumatism, rheumatoid arthritis, diabetes, heart failure, cardiovascular diseases, thrombosis, neurogenerative diseases or impaired pregnancies can be identified, and respective treatments can be indicated by the present invention.

Further, disorders of iron metabolism can be diagnosed with the method according to the invention in apparently healthy subjects. Patient groups, in the case of which the use of the claimed method is particularly advantageous, for example, are apparently healthy senior subjects as well as vegetarians. The information about the iron status in these groups possibly enables early suitable treatment of subjects having disorders of iron metabolism, already at a time when they still appear to be healthy.

Group (B) indicating iron overloading includes haemochromatosis such as sickle cell anemia or HFE gene modifications.

The invention is elucidated in the following on the basis of particularly preferred embodiments; however, it should be noted that the inventive procedure is not limited to the parameters mentioned as examples.

In a first preferred embodiment sTfR is determined as parameter (ii). Surprisingly it was found that the soluble transferrin receptor (sTfR) is a parameter for the following three types of iron status:

(a) haemoglobin synthesis rate,
(b) repletion status of the iron stores (ferritin) and
(c) non-ferritin iron deposition (disturbance in distribution, iron deposition).

In addition it is preferred that the ferritin content is determined as parameter (i). A combination of sTfR and ferritin yields information on the depletion of iron stores, haemoglobin synthesis and iron deposition as shown in FIG. 1.

These two parameters for determining the iron status i.e. sTfR and ferritin can now be combined in a preferred embodiment of the method according to the invention with a further biochemical marker or a haematological marker.

The inflammation marker CRP or the marker SAA and most preferably the marker CRP is used as the biochemical marker.

This combination can serve in particular as diagnostic markers for chronic anaemias (ACD) in rheumatic diseases.

In order to efficiently differentiate between the anaemias, the classification is carried out by calculating the ratio of sTfR/log ferritin. It is standardized on the basis of the CRP value. For the graphic representation the ratio of sTfR/log ferritin is plotted on the X axis and the CRP value is plotted on the Y axis. This results in the following classification into the various types of iron status shown in Table 1.

TABLE 1

Differentiation and treatment recommendations for various anaemias using sTfR, ferritin and CRP values

| Quadrant* | Ferritin [µg/L] | sTfR [mg/L] | sTfR/ log ferritin | CRP [mg/L] | Comments |
|---|---|---|---|---|---|
| A | >30 ♂<br>>15 ♀ | high ↑<br>(measure of erythropoietic activity) | <3.4 ♂<br><3.7 ♀ | >5<br>>5 | disturbances of iron distribution<br>disturbances of iron utilization with acute phase reaction (EPO therapy) |
| B | >400 ♂<br>>150 ♀ |  | <0.9 ♂<br><0.9 ♀ | <5<br><5 | iron overloading<br>(blood letting therapy) |
| C | 30-400 ♂<br>15-150 ♀ | <5<br>1.9 to 4.4 | <3.4 ♂<br><3.7 ♀ | <5<br><5 | normal iron status, no acute phase reaction |
| D | <30 ♂<br><15 ♀ | >5<br>>4.4 | ≧3.4 ♂<br>≧3.7 ♀ | <5<br><5 | deficiency of stored iron, no acute phase reaction (iron substitution) |
|  | <30 ♂<br><15 ♀ | very high ↑↑<br>(measure of iron requirements of the cells) | ≧3.4 ♂<br>≧3.7 ♀ | >5 | deficiency of stored iron with acute phase reaction (iron substitution) |

*see FIG. 2

The cut-off values shown in Table 1 are derived from the reference ranges for women (premenopausal) for sTfR of 1.9 to 4.4 mg/l, ferritin of 15 to 150 µg/l and CRP of <5 mg/l and for men for sTfR of 2.2 to 5.0 mg/l, ferritin of 30 to 400 µg/l and CRP of <5 mg/l. When this is represented graphically results in four quadrants which are defined by the cut-off values for CRP of 5 mg/l and for the ratios sTfR/log ferritin of 3.4 (men) and 3.7 (women) and 0.9. This enables anaemias which are caused by perturbations of iron distribution (A), iron deficiency (D) and iron overloading (B) to be distinguished from the normal iron status (C).

In a particularly advantageous embodiment of the invention the differential diagnosis of the important disorders of iron metabolism is assisted by a software program which enables a mathematical linkage of the three above-mentioned independent parameters. The following independent parameters are preferably used:

(i) ferritin as a parameter that allows an estimate of the actual body iron stores (depot iron),
(ii) sTfR as a parameter which allows an estimation of the erythropoietic activity (functional iron) and
(iii) CRP as a parameter for the diagnosis of unspecific disorders of iron metabolism which are caused for example by inflammatory processes.

In this manner the method according to the invention enables disorders of iron metabolism to be described by using the iron storage protein ferritin and the soluble transferrin receptor as an indicator for the iron requirements of the cells. In addition the determination of the soluble transferrin receptor enables an estimate of the erythropoietic activity. CRP acts as an indicator of a persistent acute phase reaction. The correlation between CRP and the ratio of sTfR/log ferritin allows an efficient differential diagnosis of anaemias such as iron deficiency, iron distribution disorders and iron overloading from normal iron status. The differential diagnosis can be further simplified for the user by a computer-aided evaluation program.

A latex-enhanced immunoturbidimetric assay can for example be used to determine the soluble transferrin receptor for use in a method in combination with the determination of ferritin and CRP. The values for sTfR stated herein in connection with methods using sTfR, ferritin and CRD refer to values measured with latex-enhanced immunoturbidimetric assays. The latex-enhanced immunoturbidimetric assay have an adequately sensitive measuring accuracy for detecting the relatively low concentrations of soluble transferrin receptor in the blood plasma (<10 mg/l, or <100 nmol/l). Since international reference methods and reference preparations are not yet available for sTfR, reference intervals on the COBAS INTEGRA® and Roche/Hitachi were determined for the test described herein and the sTfR reference range was 2.2 to 5.0 (2.5 to 97.5 percentile) for men and 1.9 to 4.4 for women.

According to the invention the cut-off value for sTfR/log ferritin which discriminates between the iron status of iron overloading and normal iron status is 0.7 to 1.4, in particular 0.8 to 1.0 and most preferably 0.9. The cut-off value with which iron deficiency can be distinguished from iron distribution disorders and normal iron status is preferably 3.0 to 4.0, more preferably 3.4 to 3.7 and most preferably at about 3.4 for men and at about 3.7 for women. Calibration to determine these values was made as described by S. Kolbe-Busch et al., Clin. Chem. Lab. Med. 40(5) (2002), 529-536. sTFR from placenta was used as standard thereby. The cut-off value for CRP above which an acute phase reaction is defined, is preferably at about 1 to 10 mg/l, more preferably at 4 to 6 mg/l and in particular at about 5 mg/l.

In a further most preferred embodiment a haematological parameter is determined as parameter (iii) and in particular the proportion of hypochromic red blood cells (HRC %) or the haemoglobin content of reticulocytes (CHr). It was surprisingly found that these parameters are new indicators for functional iron deficiency. These parameters can be used in addition to biochemical markers such as ferritin, transferrin saturation (TfS) and transferrin receptor (TfR) to identify an iron deficiency (ID).

The haematological parameters show rapidly and directly any change in erythropoietic activities.

Non-anaemic patients without APR (acute phase reaction) have a CHr of $\geq$28 pg and HCR of $\leq$5%. Patients with a CHr of <28 pg or a HCR of >5% were classified as functionally iron deficient. Serum ferritin, TfS, TfR and the calculated parameters TfR-F index (ratio TfR/log ferritin) and Tf-Tf-R product enable a reliable diagnosis of iron deficiency in comparison with HCR % and CHr in patients without APR. In the case of anaemias without APR which are often observed in infections, inflammation or tumours, the diagnostic effectiveness of the said biochemical markers ferritin and transferrin receptor is often inadequate. A combination of these biochemical markers with haematological markers such as CHr considerably improves the results. When CHr is plotted against the TfR-F index or against the Tf-TfR product, it is possible to classify anaemias in patients with and without APR inter alia into the following categories: no functional iron deficiency, functional iron deficiency combined with depleted iron stores and functional iron deficiency combined with replete iron stores.

This embodiment of the invention enables an identification of iron deficiency and a distinction of iron deficiency from other disorders of iron metabolism, in particular so-called anaemias, from chronic diseases (ACD) which accompany infections, inflammation or tumours. ACD is characterized by an inadequate erythropoietin production, inhibition of the proliferation of erythrocyte precursor cells in the bone marrow and disturbances of iron utilization. As in iron deficiency anaemia (IDA), functional iron deficiency in ACD is one of the main distinguishing factors from erythropoiesis. It is defined as an imbalance between iron requirements in the erythroid bone marrow and iron supply which is not sufficient to ensure a normal haemoglobination of red blood cells. This results in a reduced haemoglobin concentration in reticulocytes and erythrocytes. In IDA the iron supply depends on the content of the iron stores, and in the case of ACD on the rate of its mobilization. In ACD a functional iron deficiency can occur even in the presence of large iron stores if the iron release is impaired.

The diagnosis of a functional iron deficiency is important for the correct treatment of the patients. However, in practice it is often only possible to classify the patients as iron deficient, non-iron deficient or potentially iron-deficient. The third group of patients which are typically those with an acute phase reaction (APR) or a cancer related anaemia (CRA) have previously required an examination of their bone marrow in order to determine the type of disease.

Usually biochemical markers of iron metabolism are used such as serum or plasma iron, transferrin, % transferrin saturation (TfS), ferritin and serum-circulating transferrin receptor (TfR). The diagnosis of IDA is based on the presence of anaemia and morphological features of erythrocytes (hyperchromia, mycrocytosis) in conjunction with a low serum ferritin and a reduced transferrin saturation. The diagnosis of ID in conjunction with normal serum ferritin contents may, however, be difficult in the case of ACD. Ferritin is an acute phase reactant, transferrin is a negative acute phase reactant and the concentration of both proteins is influenced by various conditions. An increase in TfR which is a useful indicator for iron deficiency, can also occur in patients with an increase in the number of red precursor cells in the bone marrow. Due to these difficulties it is necessary to provide clinical laboratory tests which measure the functional availability of iron for haemoglobin synthesis especially in the red blood cells and their precursors.

A marker which can be used to assess the functional iron status, is the measurement of the proportion of hypochromic red cells (HRC %). Due to the life time of erythrocytes of about 120 days, HCR % integrates information over a long period and is thus a late indicator for iron-limited erythropoiesis. A value for HCR of <10% in conjunction with low serum ferritin indicates that the iron supply for erythropoiesis is sufficient to enable a normal haemoglobination of red cells.

The cellular haemoglobin content of reticulocytes (CHr) is an early marker for functional iron deficiencies since reticulocytes exist in the circulation for only 1 to 2 days. The utility of this index for monitoring the erythropoietic function in order to assess the iron status, to diagnose an iron deficiency and to diagnose and treat various haematological diseases is known.

A combination of the haematological indices HRC % or/and CHr with biochemical markers is described here for the first time.

Using the 2.5 and 97.5 percentiles of the control group, the following cut-offs were determined for the present invention: 3 to 7%, in particular 4 to 6% and most preferably about 5% for HCR and 25 to 30 pg, in particular 27 to 29 pg and particularly preferably about 28 pg for CHr. The iron status can preferably be classified using a diagnostic plot in which CHr is plotted against TfR-F or against Tf-Tf-R. In this manner the iron status can be divided into various categories and in particular four categories i.e. normal iron status, iron deficiency (CRP normal), iron deficiency (CRP increased) and iron distribution disorder.

In a further preferred embodiment the invention relates to a method for determining the iron status and, in particular, for detecting disorders of iron metabolism comprising the determination of
  (i) a parameter which allows determination of the total body iron stores,
  (ii) a parameter which allows determination of the erythropoietic maturation process and/or its activity,
  (iii) a parameter which allows determination of unspecific disorders of iron metabolism, in particular, a biochemical parameter, and
  (iv) a haematological parameter, in particular, MCH or CHr.

In this embodiment group (A) concerning patients who probably have disturbances of iron distribution (acute deficiency of functional iron) can be further divided in two groups. In particular, patients having no acute deficit of functional iron can be distinguished from patients actually having functional iron deficiency or disturbance of iron distribution. MCH or CHr can be determined from blood count. MCH is the average hemoglobin content of an erythrocyte cell and is reduced, if an acute deficiency of functional iron and thus a disturbance of iron distribution occurs. Therefore, MCH can be used to distinguish a deficiency of functional iron from other conditions. 28 pg/cell is to be regarded as a limiting value of MCH and CHr, whereby no acute deficiency of functional iron is the case for values above that value and deficiency of functional iron is diagnosed, if values are lower.

The invention further relates to a test strip for performing the inventive method. Such a test strip comprises means for the determination of
  (i) a parameter which allows determination of the total body iron stores,
  (ii) a parameter which allows determination of the erythropoietic maturation process and/or its activity, and
  (iii) a parameter which allows determination of unspecific disorders of iron metabolism.

In a preferred embodiment, for example, CRP will be determined competitively and the other two parameters by using a sandwich assay.

The invention is further elucidated by the attached figures and examples.

EXAMPLES

Example 1

163 patients were examined using the parameters CRP and sTfR/log ferritin and classified according to the results obtained as normal iron status, iron deficiency, iron distribution disturbance or iron overloading. The combined determination of the three parameters sTfR, ferritin and CRP proved to be highly suitable for differential diagnosis.

Example 2

373 patients were examined using a combination of haematological parameters and biochemical parameters and classified into four groups. Group N is the control group and contained non-anaemic patients without APR. Group A consists of anaemic patients without APR. Group M contains anaemic patients with APR in combination with CRA, ACD or an acute infectious or inflammatory disease. The patient group NA contains non-anaemic patients with APR.

Ferritin was determined on a Cobascore analyzer from Roche Diagnostics, Mannheim, Germany and the reference range was determined as 20 to 150 µg/l for women and 20 to 350 µg/l for men. TfR was determined in each sample using commercial assays. The analytical principle of the assay is based on microagglutination of latex particles which are coated with a monoclonal anti-TfR antibody (Dade Behring, Marburg, Germany). In this manner a latex-enhanced nephelometric test is carried out. The reference range (2.5 to 97.5 percentile) was 0.4 to 1.8 mg/l.

TfS was calculated using the formula TfS(%)=Fe(µg/l)× 7.09/Tf(g/l).

In order to determine disorders of iron metabolism CHr and HRC % were determined as indicators of an iron deficient erythropoiesis as a plot against the TfR-F index. The following results were obtained for the individual patient groups.

N group (non-anaemic group without APR)

The control group consisted of 71 patients which were found in quadrant 1 (left top, FIG. 3) in the diagnostic blots comprising 4 quadrants.

A group (anaemic group without APR)

Figure 3:
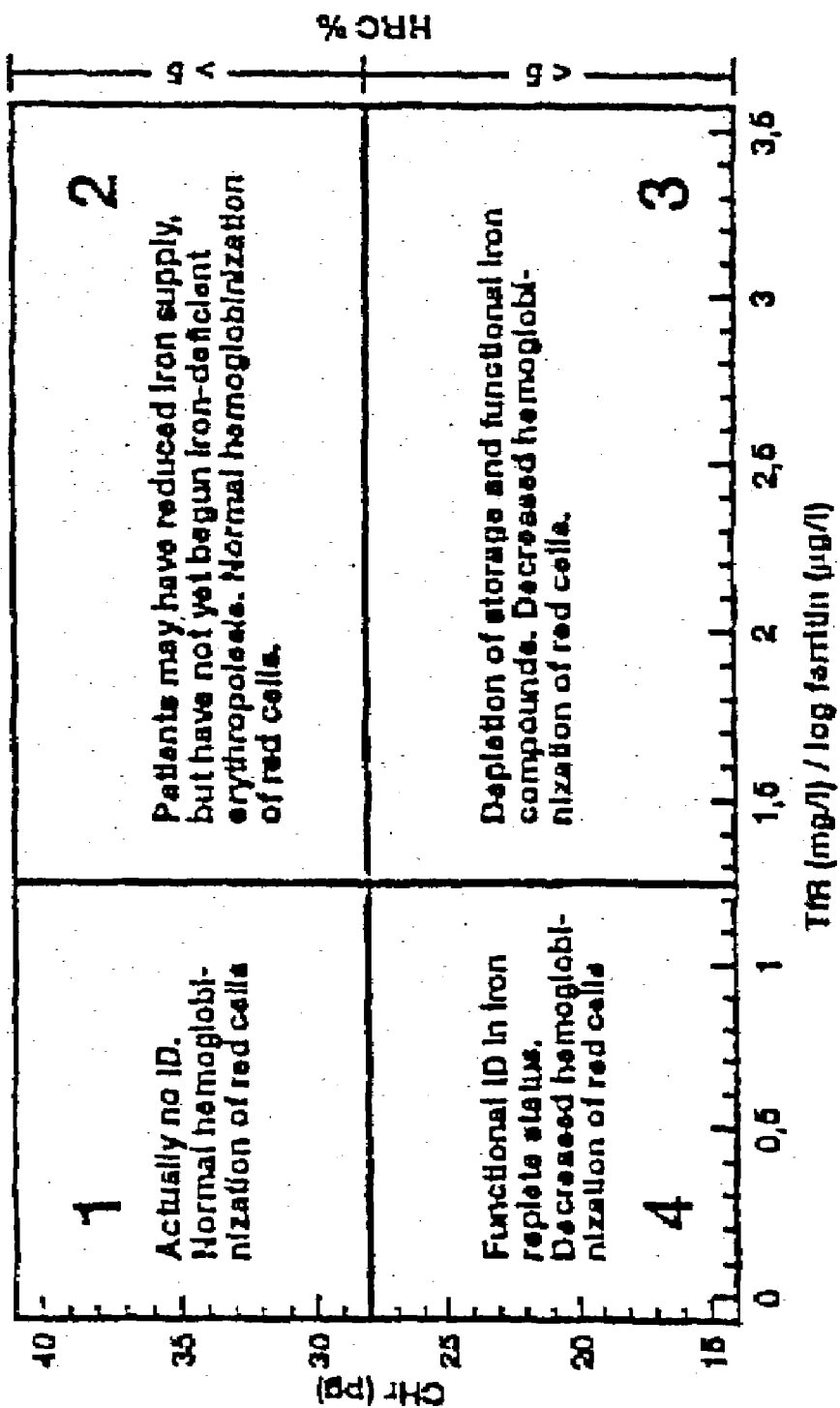
FIG. 3 shows the classification used in a combination of haematological and biochemical markers.
Figure 4:
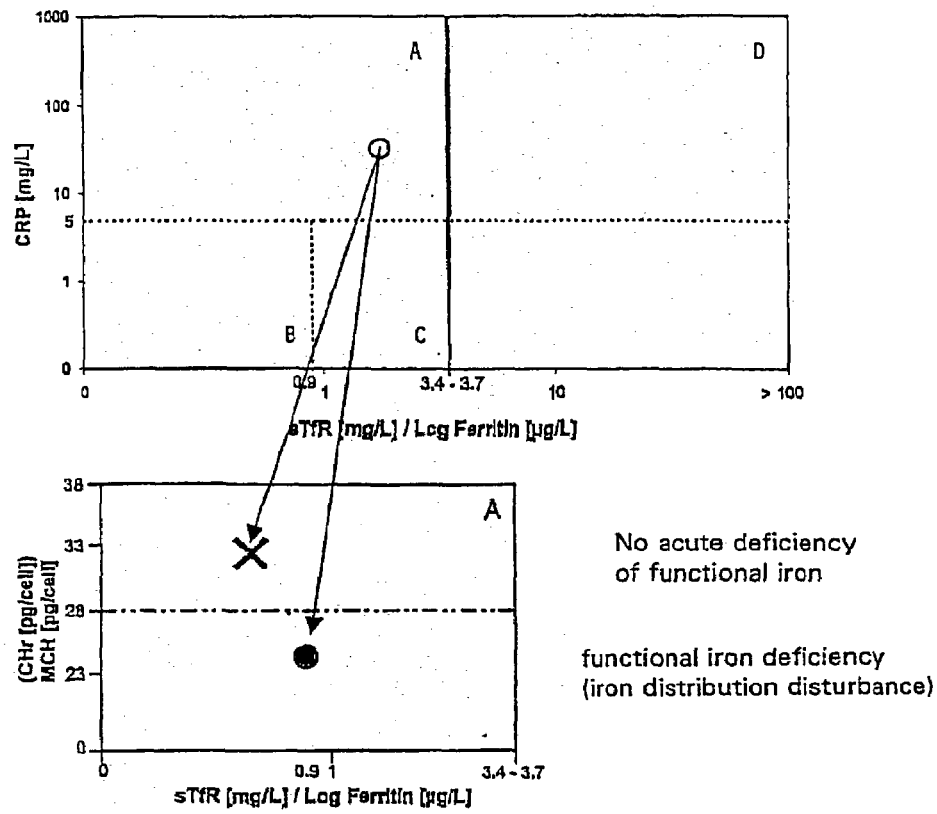
FIG. 4 shows a preferred embodiment according to the invention, wherein group (A) is further divided by determination of a haematological parameter, in particular, of MCH or CHr.
Figure 5:
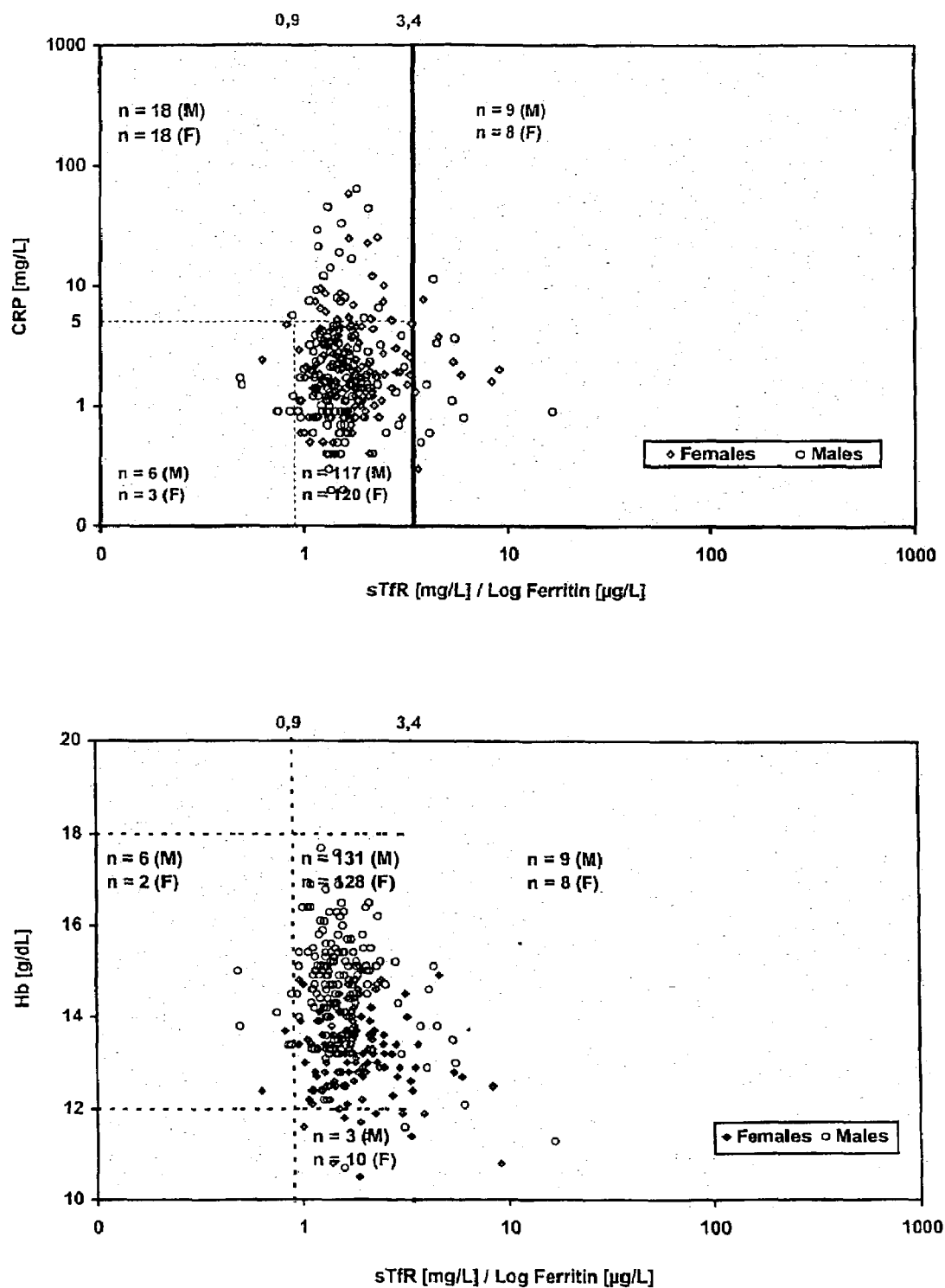
FIG. 5 shows results of a determination of ferritin, the soluble transferrin receptor and CRP and hemoglobin, respectively.

79 anaemic patients without APR were examined and assigned to quadrant 2 (FIG. 3).

NA group (non-anaemic group with APR)

This group consisted of 80 patients which were classified in quadrant 4 (FIG. 3).

AA group (anaemic group with APR)

This group consisted of 143 patients which were classified in quadrant 3 (FIG. 3).

Patients with data points in quadrant 1 had a CHr of $\geq 28$ pg.

Patients in quadrant 2 are iron-deficient according to the TfR-F index. All patients in this quadrant have a CAA and HRC>5%. The pattern CHr>288 pg, HRC>5%, elevated TfR and normal or elevated ferritin indicated that these patients with CRA and APR have a reduced iron supply as indicated by the increase in TfR which, however, was not sufficient to cause a functional iron deficiency.

Patients with data points in quadrant 3 had the lowest ferritin and highest Tf concentrations. Tf is a negative acute phase reactant and the mean concentration was reduced in patients with an iron replete status in quadrants 1 and 4. In patients of quadrant 3 with haematological and biochemical identified iron deficiency, APR did not, however, cause a decrease in the serum Tf which indicates that the positive stimulus of iron deficiency is larger than the negative stimulus of APR on Tf synthesis.

The patients with data points in quadrant 4 had a CHr of <28 pg and a HRC of >5%.

In summary this means that the allocation of the data points to one of the quadrants 1 to 4 in the diagnostic plot denotes the following for the identification of iron deficiency in the diagram CHR against TfR/log ferritin:
  Quadrant 1: no biochemical or haematologically identified iron deficiency
  Quadrant 2: only biochemically identified iron deficiency
  Quadrant 3: biochemically and haematologically identified iron deficiency
  Quadrant 4: only haematologically identified iron deficiency.

The patient groups can be subdivided as follows according to the haematological and biochemical results:

Group N: non-anaemic, no APR; Hb (men)$\geq$140 g/l, Hb (women)$\geq$123 g/l, CRP$\leq$5 mg/l, WBC$\leq$10,000/µl, ESR (erythrocyte sedimentation rate)$\leq$30 mm/h, RDW (red cell distribution width)$\leq$15%;

Group A: anaemic, no APR; Hb (men)<140 g/l, Hb (women)<123 g/l, CRP≦5 mg/l, WBC≦10,000/µl; ESR≦30 mm/h;

Group NA: non-anaemic with APR; Hb (men)≧140 g/l, Hb (women)≧123 g/l, CRP>5 mg/l or WBC>10,000/µl or ESR>30 mm/h or RDW>15%;

AA: anaemic with APR: Hb (men)<140 g/l, Hb (women) <123 g/l, CRP>5 mg/l or WBC>10,000/µl or ESR>30 mm/h.

Example 3

Functional and Manifest Iron Deficiency in Apparently Healthy Senior Subjects

Example 3 shows the results of a determination of disorders of iron metabolism in apparently healthy senior subjects. To evaluate disorders in seniors (age 50-80 years) 283 apparently healthy subjects of 5 doctors' offices were examined.

Based on interviews, 283 apparently healthy subjects were identified. Additionally the following clinical parameters were determined: ALT, GGT, Creatinine, fasting Glucose, Uric Acid, Cholesterol, TSH, FT4, NT-proBNP, blood cell count (Hb, MCV, MCH). 36 out of 139 females were under a hormone-therapy. sTfR varied in the range of 1.9-4.5 mg/L, median 3.1 mg/L. 104 patients showed Ferritin values <400 µg/L, 103 patients had Ferritin-values >400 µg/L. Hb-values varied from 10.5 g/dl to 17.7 g/dl, the median was at 14.0 g/dl. 54 patients had CRP values <5 mg/L. CRP values >5 mg/L were found in 153 patients.

Using mathematical relationships between three independent parameters, the laboratory diagnostics of the main disturbances or iron metabolism can be supported using a software program.

TABLE 2

Determined values of the parameters depicted as total group as well as divided in female and male subjects, respectively.

|  | CRP [mg/L] | Hb [g/dL] | sTfR [mg/L] | Ferritin [ng/mL] | sTfR [mg/L]/log Ferritin [µg/L] |
|---|---|---|---|---|---|
| Total Group |
| n | 305 | 303 | 305 | 305 | 305 |
| min | 0.2 | 10.5 | 0.9 | 3.5 | 0.5 |
| max | 64.2 | 17.7 | 11.3 | 1222 | 16.6 |
| mean | 3.6 | 14.0 | 3.4 | 163.9 | 1.8 |
| median | 1.7 | 14.0 | 3.2 | 112.6 | 1.5 |
| perc(2.5) | 0.4 | 11.6 | 1.9 | 11.2 | 0.9 |
| perc(97.5) | 25.0 | 16.4 | 5.7 | 641.0 | 5.3 |
| Females |
| n | 155 | 155 | 155 | 155 | 155 |
| min | 0.3 | 10.5 | 1.2 | 4 | 0.6 |
| max | 58.9 | 15.1 | 10.2 | 1060 | 9.0 |
| mean | 3.3 | 13.3 | 3.4 | 112 | 1.9 |
| median | 1.8 | 13.4 | 3.2 | 87 | 1.7 |
| perc(2.5) | 0.4 | 11.4 | 1.9 | 12 | 1.0 |
| perc(97.5) | 22.9 | 14.9 | 5.6 | 465 | 5.4 |
| Males |
| n | 150 | 149 | 150 | 150 | 150 |
| min | 0.2 | 10.7 | 0.9 | 4 | 0.5 |
| max | 64.2 | 17.7 | 11.3 | 1222 | 16.6 |
| mean | 3.9 | 14.7 | 3.4 | 217 | 1.7 |
| median | 1.5 | 14.9 | 3.2 | 174 | 1.4 |
| perc(2.5) | 0.4 | 11.6 | 1.9 | 11 | 0.7 |
| perc(97.5) | 33.8 | 16.9 | 6.6 | 677 | 5.3 |

The iron status was differentiated by the calculation of the quotient of sTfR/log Ferritin. CRP discriminates inflammatory from non-inflammatory processes. The following cut-off values are proposed by experts:

| | |
|---|---|
| sTfR for patients with iron deficiency (w, m): | 4.4 and 5 mg/L |
| Ferritin for patients with iron deficiency (w, m): | 15 and 30 µg/L |
| Ferritin for patients with iron overload (w, m): | 150 and 400 µg/L |
| CRP for patients with persistent acute phase reaction: | >5 mg/L |

Disorders of iron distribution can be described using Ferritin, the iron storage protein and the soluble Transferrin Receptor, an indicator for cellular iron demand. Additionally, erythropoietic activity can be estimated by determining the soluble Transferrin Receptor. CRP acts as an indicator of persistent acute phase reaction.

Figure 6:
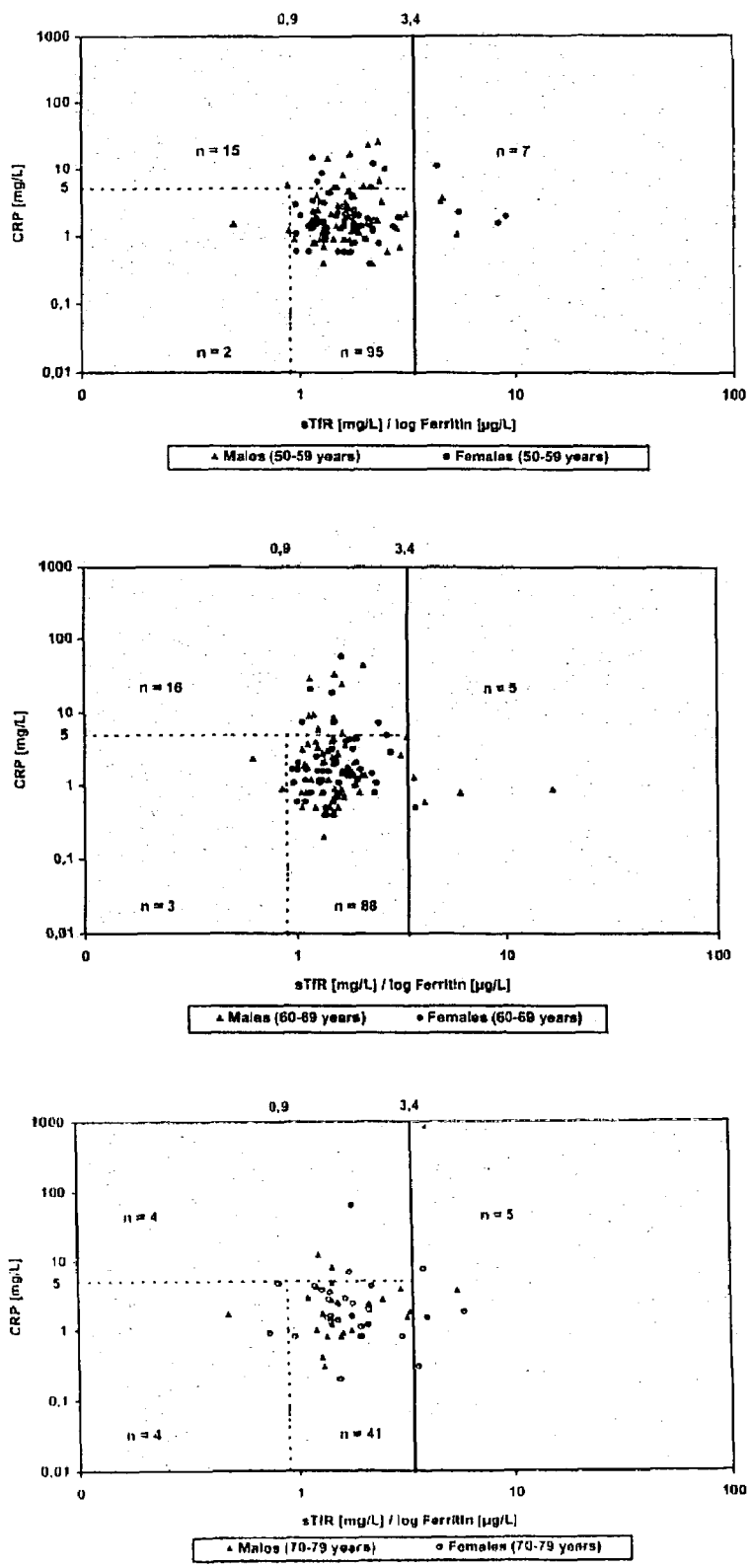
FIG. 6 shows the results of the determination of disorders of iron metabolism in apparently healthy seniors, divided in age groups.
Figure 7:
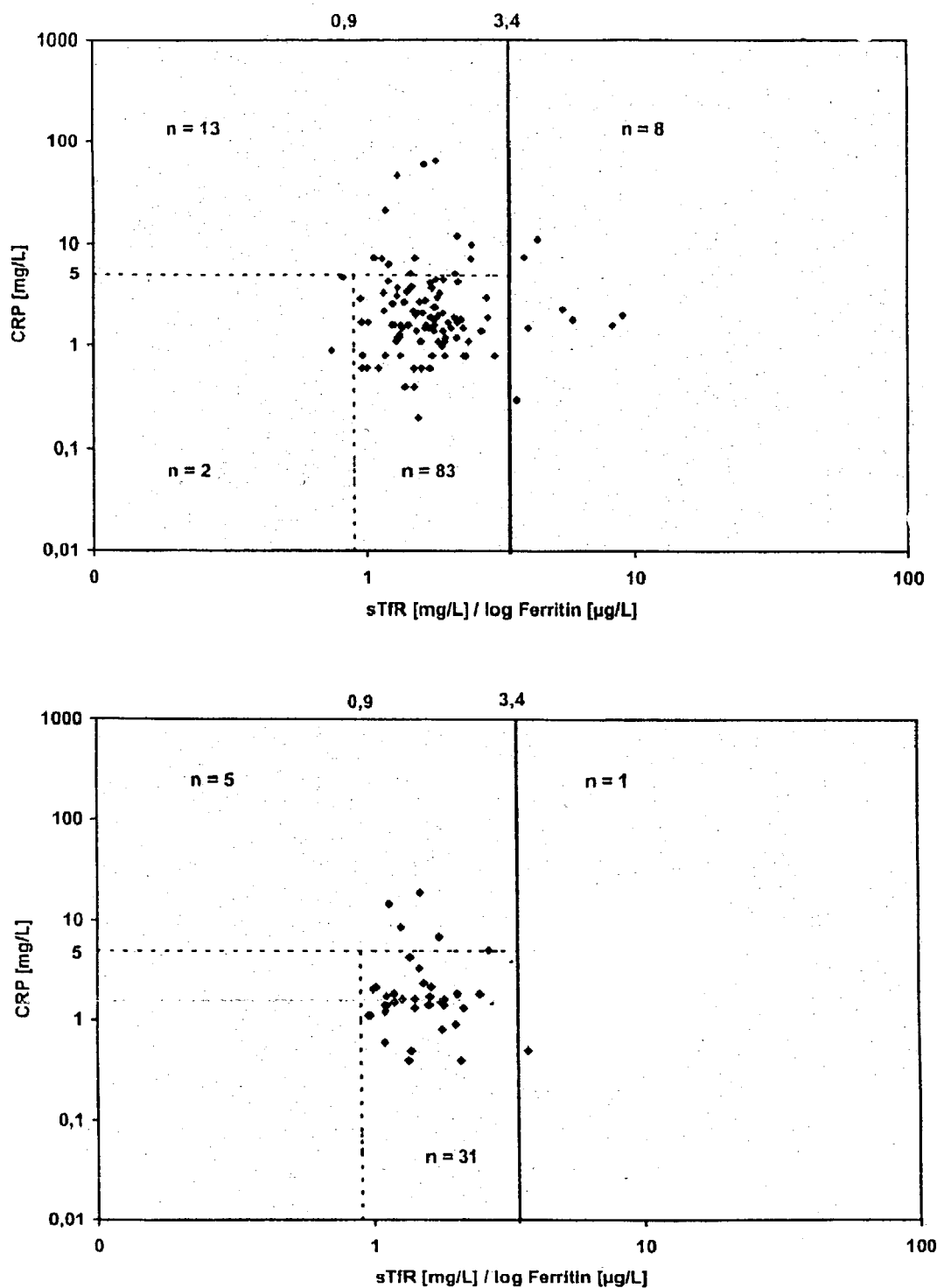
FIG. 7 shows the results of determination of disorders of iron metabolism in apparently healthy female seniors without and with hormone substitution therapy.

The determination revealed that approximately 26% (72 subjects) of the investigated 283 apparently healthy seniors showed a functional iron deficiency. 7% (19 subjects) suffered from manifest iron deficiency. The results are statistically independent from the age and from the hormone therapy, as can be seen from FIG. 6 and FIG. 7.

Example 4

Treatment of Anemia in Rheumatoid Arthritis

The anemia of chronic disease (ACD) occurs in association with chronic inflammation of infectious processes. Treatment with recombinant human erythropoietin (r-HuEPO) has proven successful in improving anemia in patients with ACD. Kaltwasser et al. [J. Rheumatol. 28:2430-2437] showed that r-HuEPO in combination with intravenous iron administration is effective in correcting ACD in patients with inflammatory active rheumatoid arthritis (RA).

Measurement of disorders of iron metabolism in this study was done using ferritin, the iron storage protein and the soluble transferrin receptor, an indicator for cellular iron demand and erythropoietic activity. CRP acts as an indicator of persistent acute phase reaction.

By determining the three independent parameters CRP, sTfR and Ferritin, the main disturbances of iron metabolism can be screened and monitored. The blood count (Hb, Hct, erythrocytes, MCV, $CH_R$) was determined separately.

The study was designed as an open 24 week single center study with a maximum treatment period of 12 weeks. 28 of 30 patients with RA were enrolled. Patients were treated with 150 IU/kg r-HuEPO NeoRecormon subcutaneously twice weekly for a maximum of 12 weeks. In case of functional Iron deficiency the patients additionally received 200 mg iron-sucrose i.v. per week.

Patients were evaluated every 2 weeks during treatment period and monthly for 3 months after the end of r-HuEPO treatment. A blood sample was taken at every visit.

Thirty patients (27 women, 3 men; age range 22-77 years) were enrolled in the study. Based characteristics of patients are shown in Table 3.

TABLE 3

Baseline characteristics of patient population

| Patient | Age (years) | Sex | Disease Duration (years) | DMARD | Steroid | RF | Hb | IV iron |
|---|---|---|---|---|---|---|---|---|
| 1 | 60 | F | 27 | MTX | 15 | − | 7.4 | — |
| 2 | 60 | F | 2 | — | 5 | − | 9.7 | 0.8 |
| 3 | 60 | F | 13 | — | 15 | + | 10.7 | — |
| 4 | 38 | F | 23 | — | 6 | − | 10.1 | 1.6 |
| 5 | 73 | F | 4 | — | 7.5 | + | 12.1 | — |
| 6 | 61 | F | 9 | MTX | 20 | + | 7.2 | 2.4 |
| 7 | 66 | F | 16 | MTX | 15 | + | 10.6 | 1.4 |
| 8 | 55 | F | 7 | MTX | 5 | − | 11.8 | 0.8 |
| 9 | 68 | F | 4 | MTX | 7.5 | − | 12.1 | 0.2 |
| 10 | 58 | M | 16 | MTX | 7.5 | + | 11.5 | 0.4 |
| 11 | 62 | M | 9 | MTX | 10 | + | 12.2 | 1.2 |
| 12 | 56 | F | 3 | MTX/SSZ | 10 | + | 10.9 | 0.8 |
| 13 | 60 | M | 19 | CSA | 6 | + | 12.4 | — |
| 14 | 40 | F | 10 | SSZ | 5 | − | 9.7 | 1.2 |
| 15 | 65 | F | 7 | — | 5 | + | 9.8 | 0.4 |
| 16 | 45 | F | 1 | MTX | 10 | + | 11.2 | 1.0 |
| 17 | 35 | F | 14 | MTX | 10 | + | 10.2 | 0.6 |
| 18 | 38 | F | 1 | AZA/SSZ | — | − | 11.5 | 0.8 |
| 19 | 77 | F | 4 | SSZ | 5 | + | 10.8 | — |
| 20 | 58 | F | 50 | MTX | 10 | − | 10.1 | 1.2 |
| 21 | 65 | F | 2 | SSZ | 12.5 | + | 10.5 | 1.0 |
| 22 | 36 | F | 12 | MTX | — | + | 10.1 | 1.0 |
| 23 | 31 | F | 1 | AZA | 10 | − | 11.2 | 0.4 |
| 24 | 25 | F | 2 | HCQ | 5 | − | 11.2 | 1.0 |
| 25 | 74 | F | 4 | MTX | 5 | − | 10.8 | 0.8 |
| 26 | 28 | F | 4 | SSZ | 2.5 | − | 11.9 | 0.4 |
| 27 | 48 | F | 13 | MTX/SSZ | 5 | + | 11.4 | 0.4 |
| 28 | 55 | F | 6 | — | 12.5 | + | 10.1 | — |
| 29 | 72 | F | 24 | — | 10 | − | 9.6 | 0.6 |
| 30 | 22 | F | 1 | SSZ | — | − | 10.5 | 0.4 |
| Mean | 53 | | 10 | | 9 | | 10.6 | 0.7 |
| Range | 22-77 | | 1-50 | | 0-20 | | 7.2-12.4 | 0-2.4 |

MTX: methotrexate; SSZ: sulfasalazine; CSA: cyclosporine A; AZA: azathioprine; HCQ: hydroxychloroquine; DMARD: disease modifying antirheumatic drugs The median hemoglobin (Hb) concentration at baseline was 10.7 g/dL. (range 7.2-12.4). 22 patients received DMARD, 8 patients were DMARD-naive during the study. 27 patients were treated with low dose steroids (range 5-20 mg/day prednisolone). 28 of 30 patients completed the treatment and follow-up period.

Deep-frozen (−70° C.) serum samples of 28 patients completing the study were investigated. The patients having an initial Hb≦10 g/dL showed a rapid increase of Hb of 2.0±0.5 g/dL after 4 weeks of treatment. Ferritin decreased 21±14 μg/L after 2 weeks, sTfR concentration increased 2.1±0.4 mg/L and the sTfR/log Ferritin index increased 1.9±0.6. After termination of r-HuEPO treatment, Hb decreased in the follow-up period to 12.6±0.9 g/dL after one month and 11.6±1.1 g/dL (Ferritin 163±58 μg/L, median 170 μg/L, sTfR 7.2±3.3 mg/L, median 7.1 mg/L, sTfR/log Ferritin 2.6±1.7) three months after the end of treatment. CRP was only slightly reduced from 37±25 to 26±23 mg/L, median 21 mg/L.

Figure 8:
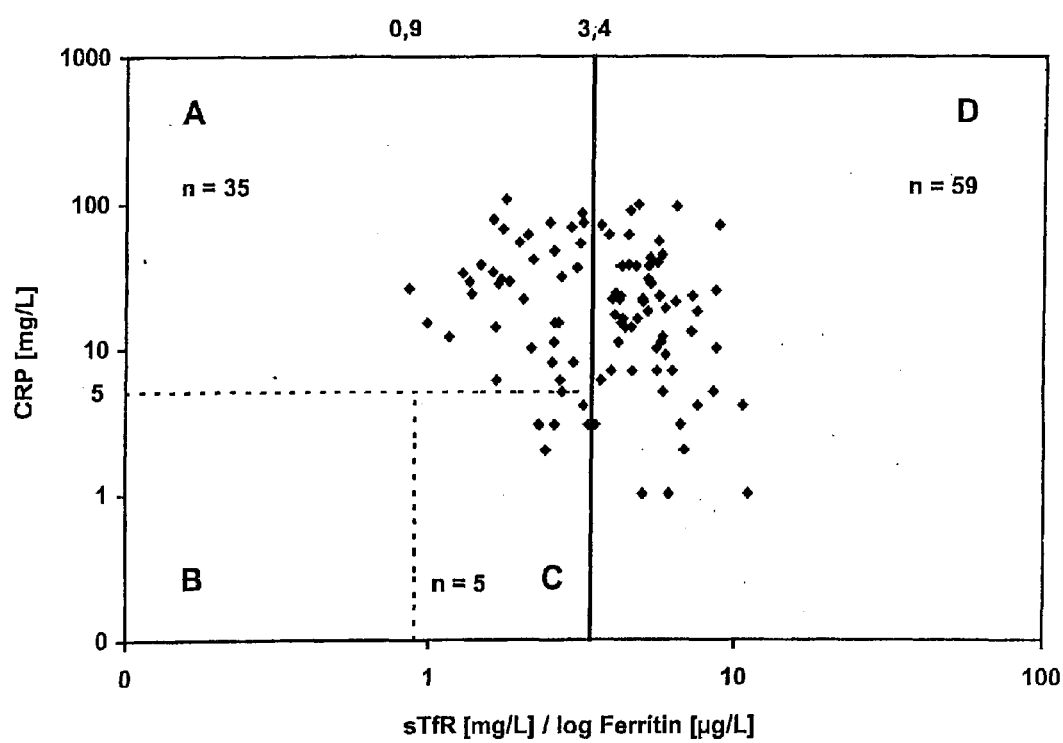
FIG. 8 shows the relationship between CRP concentration and sTfR/log ferritin in patients suffering from rheumatoid arthritis.

FIG. 8 shows the relationship between CRP concentrations and sTfR/log Ferritin in patients suffering from rheumatoid arthritis. Field A depicts a likely disturbance of iron distribution; field B an iron overload, field C a normal iron status and field D an iron deficiency.

Nonresponse to treatment was not observed in this study. Analysis of different subsets of patients showed that treatment with DMARD or the grade of anemia had no influence on the response to treatment with r-HuEPO. The reason for the rapid increase of hemoglobin in the study and the lack of nonresponders may be that the development of functional iron deficiency induced by treatment with r-HuEPO was carefully observed and appropriately corrected by i.v. iron administration. Functional iron deficiency can be easily detected by measuring serum ferritin in combination with soluble Transferrin Receptor (sTfR) in peripheral blood. In our study 82% of patients developed functional iron deficiency and therefore received i.v. iron sucrose.

Figure 9:
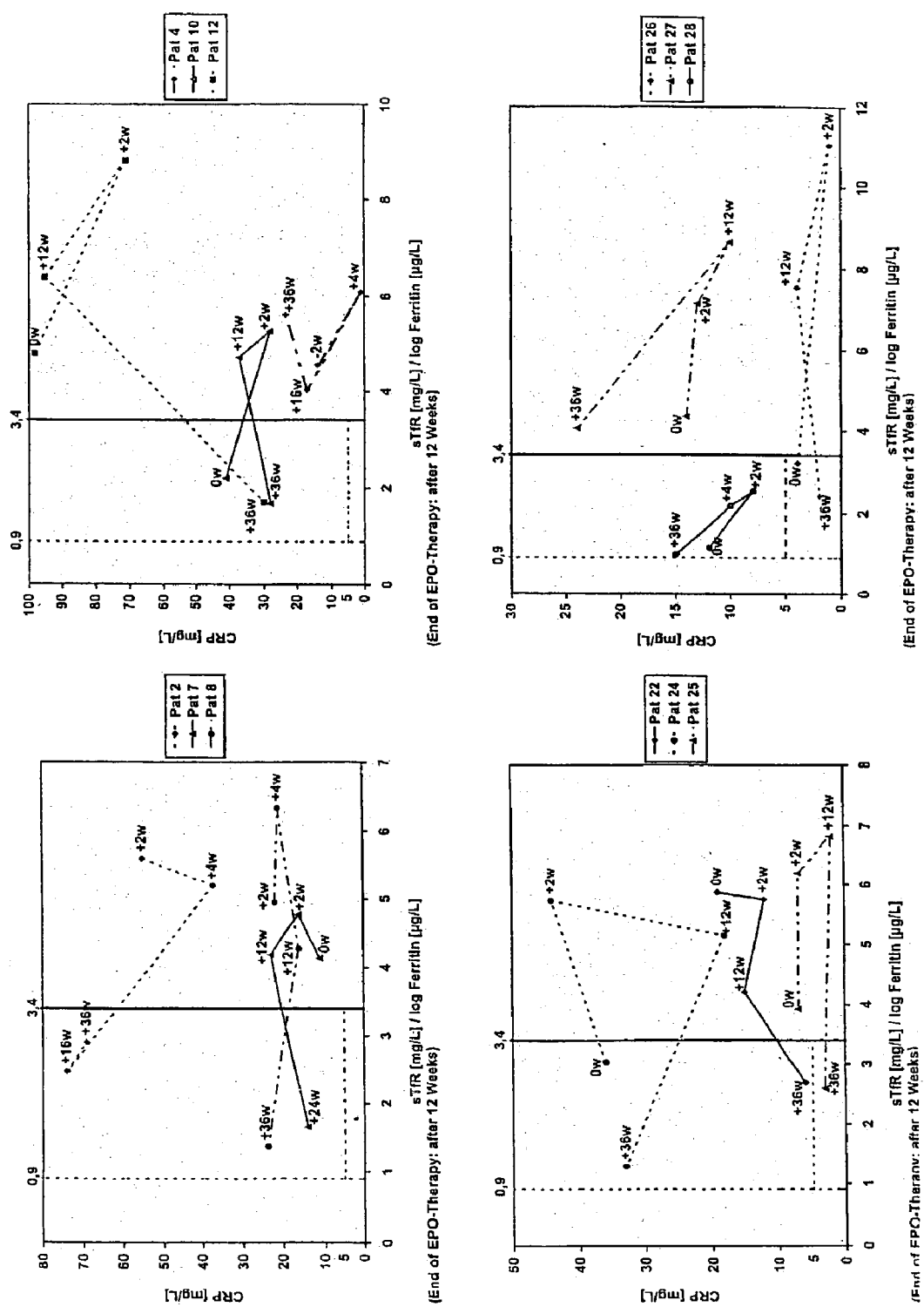
FIG. 9 shows the erythropoietic response of 12 patients with RA during administration of rHuEPO with iron.
Figure 10:
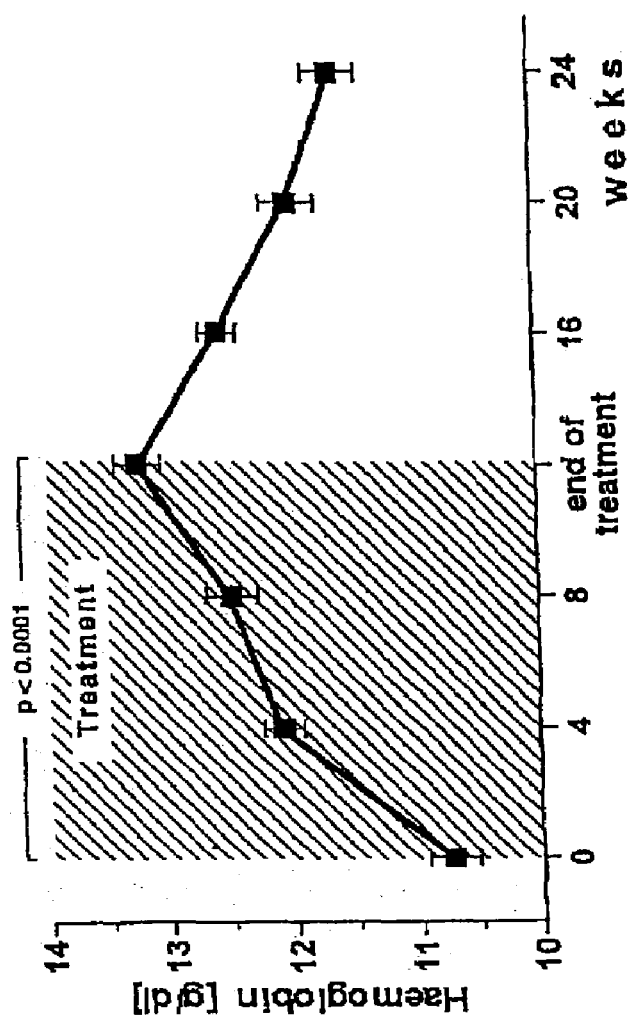
FIG. 10 shows the erythropoietic response indicated by increase of Hb during administration of rHuEPO with iron.

FIG. 9 shows the erythropoietic response of 12 patients with RA during administration of r-HuEPO with iron. FIG. 10 shows the erythropoietic response indicated by an increase of Hb during administration of r-HuEPO with iron (shaded area). Data are mean±SEM in 28 patients with RA. Weeks 12-24 are post treatment surveillance.

This study shows that anemia of chronic disease in RA patients can be successfully treated with human erythropoietin and i.v. iron. The additional supplementation with i.v. iron in case of functional iron deficiency is safe and economical and ensures an optimal hematological response. The correlation between CRP and the sTfR/log Ferritin quotients allows to perform an efficient differential diagnosis and monitoring of anemia therapy. During treatment an increase of Hb was observed. After the end of administration poor erythropoietic response indicated by decrease of Hb was found.

Example 5

Patients with Chronic Renal Diseases

The clinical finding that plasma erythropoietin is lower in uremic patients than in non-uremic patients with a comparable degree of anemia suggests that uremic anemia is caused by the inadequate production of erythropoietin by chronically diseased kidneys.

In patients with disturbances of iron utilization, the individual erythrocyte contains a normal amount of hemoglobin despite the lowering of the patient's hemoglobin value. MCH and MCV are normal. Iron deficiency is apparently not the problem in this case, but rather the erythrocyte balance between formation and decomposition. This balance is reflected in the reticulocyte count (as a measure of the regeneration of erythropoiesis).

Patients with chronic renal insufficiency, including those on chronic hemodialysis (CHD) are prime candidates for a therapy with recombinant erythropoietin (rhEPO).

The rapidity and extent of the hematocrit increase are regulated by the rhEPO dose. Poor response can be caused by an iron deficiency due to inadequate iron stores or deficient mobilization from these stores (functional iron deficiency). Further causes of a diminished ability to respond to rhEPO are a vitamin deficiency ($B_{12}$, $B_6$, Folic Acid) or a reduction in stem cells in the bone marrow.

In this study Ferritin, the Soluble Transferrin Receptor (sTfR), CRP and Homocysteine (tHYC) were determined. Ferritin is the iron storage protein, sTfR acts as an indicator for cellular iron demand and erythropoietic activity. CRP is an indicator of a persistent acute phase reaction, and elevated tHYC levels are a risk factor for development of Cardiovascular diseases. A PC-based calculation program was developed which allows to determine the relationship between CRP/Homocysteine concentration and sTfR/Log-Ferritin (sTfR-F-index). Two independent studies were carried out. For the determination of total Homocysteine, the blood was cooled on ice, serum was stored at −70° C., for no longer than 1 week before being analyzed. To avoid differences due to repeated freeze and thaw cycles, all analyses were carried out on the same day. Total Homocysteine was measured on an Abbott® IMX Analyzer (Illinois, USA) using the ion capture method and microparticle enzyme immunoassay and by a modified GC/MS-method.

207 patients on hemodialysis (age 27-82 years, 120 males, 87 females) were investigated.

1$^{st}$ Study 130 hemodialysis patients had elevated serum concentrations of Homocysteine (Reference range 5-15 µmol/L) in the range 25-97 µmol/L, median 23 µmol/L. sTfR-concentrations (Reference range: 2.0-5 mg/L (males) and 1.9-4.4 mg/L (females) varied in the range 0.8-9.8 mg/L, median 3.2 mg/L. 17 patients had an sTfR>5 mg/L. Serum-Ferritin values (reference range: 30-400 µg/L (males) and 15-150 µg/L (females) were of 58 patients within the range <400 µg/L, 80 patients with the Ferritin-values >400 µg/L. Numbers of patients with CRP-values <5 mg/L (patients without persistent acute phase reaction) was 24 and CRP-values >5 mg/L were found in 114 patients. Data are depicted in Table 4.

TABLE 4

| | CRP [mg/L] | Homocysteine [µmol/L] | sTfR [ng/mL] | Ferritin [ng/mL] |
|---|---|---|---|---|
| N | 138 | 147 | 150 | 150 |
| Min | 1.0 | 4.6 | 0.8 | 8.0 |
| Max | 201.0 | 97.0 | 9.8 | 1496.0 |
| Mean | 14.2 | 25.7 | 3.4 | 454.1 |
| Median | 8.5 | 23.2 | 3.2 | 371.5 |

2$^{nd}$ Study 72 hemodialysis patients had elevated serum concentrations of Homocysteine (Reference range 5-15 µmol/L) in the range 7-142 µmol/L, median 22 µmol/L. sTfR-concentrations (Reference range: 2.0-5 mg/L (males) and 1.9-4.4 mg/L (females) varied in the range 1.6-7.8 mg/L, median 3.4 mg/L. 14 patients had an sTfR>5 mg/L. Serum-Ferritin values (reference range: 30-400 µg/L (males) and 15-150 µg/L (females) were of 51 patients within the range <400 µg/L, 21 patients with the Ferritin-values >400 µg/L. Numbers of patients with CRP-values <5 mg/L (patients without persistent acute phase reaction) was 31 and CRP-values >5 mg/L were found in 41 patients. Data of study 2 are set forth in Table 5.

TABLE 5

| | CRP [mg/L] | Homocysteine [µmol/L] | sTfR [ng/mL] | Ferritin [ng/mL] |
|---|---|---|---|---|
| n | 72 | 76 | 72 | 76 |
| min | 0.5 | 6.8 | 1.6 | 22 |
| max | 270 | 142 | 7.8 | 1577 |
| mean | 15 | 27.5 | 3.7 | 313 |
| median | 59 | 21.6 | 3.4 | 225 |

Differentiation Using sTfR, Ferritin, CRP, Homocysteine

Hyperhomocysteinemia is frequently found in patients with end-stage renal disease. These patients have mildly to moderately elevated plasma tHCY concentrations, typically in the range of 20 to 80 µmol/L.

An efficient method for differentiating between anemias is to calculate the quotient of sTfR/log Ferritin. CRP discriminates inflammatory from non-inflammatory processes. Following cut-off values are proposed.

| | |
|---|---|
| sTfR for patients with iron deficiency (w, m): | 4.4 and 5 mg/L |
| Ferritin for patients with iron deficiency (w, m): | 15 and 30 µg/L |
| Ferritin for patients with iron overload (w, m): | 150 and 400 µg/L |
| CRP for patients with persistent acute phase reaction: | >5 mg/L |
| Homocysteine in renal patients | <20 µmol/L |

In two independent studies 207 patients with renal isufficiency (age 27-82 years) were investigated. 169 patients (except 38 patients) had elevated serum concentrations of Homocyteine in the range of 15-143 µmol/L, median 23 µmol/L. sTfR varied in the range of 0.8-9.7 mg/L, median 3.3 mg/L. Ferritin values of 104 patients were found in the range <400 µg/L, 103 patients had Ferritin values >400 µg/L. CRP values <5 mg/L were determined in 54 patients. CRP values >5 mg/L were found in 153 patients.

Figure 11A:
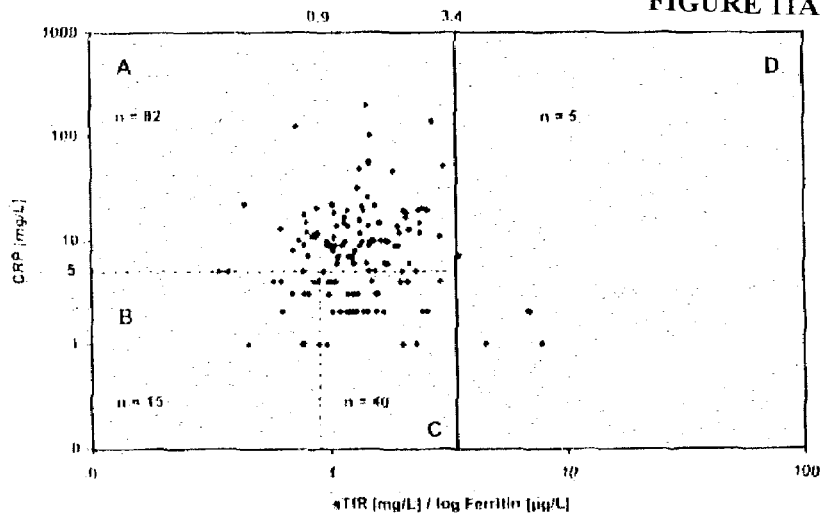
FIG. 11 shows the relationship between CRP concentration and sTfR/log ferritin in renal patients.
Figure 11B:
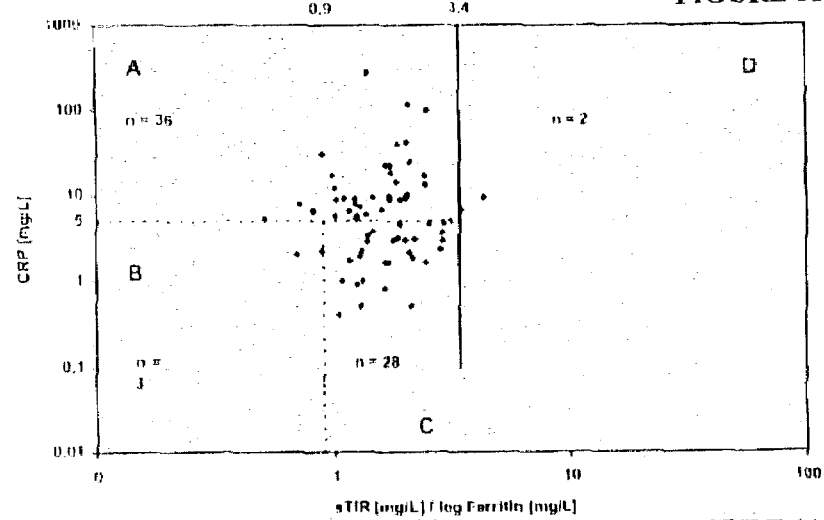
Figure 11C:
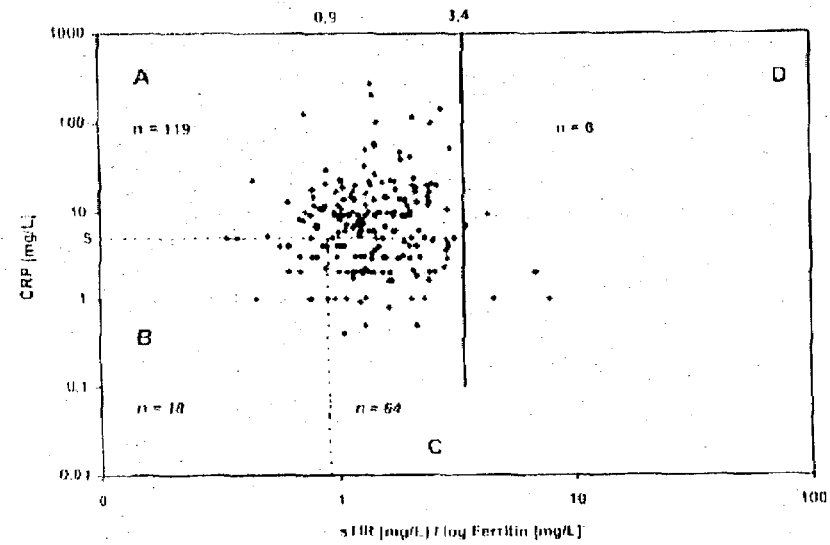
Figure 12A:
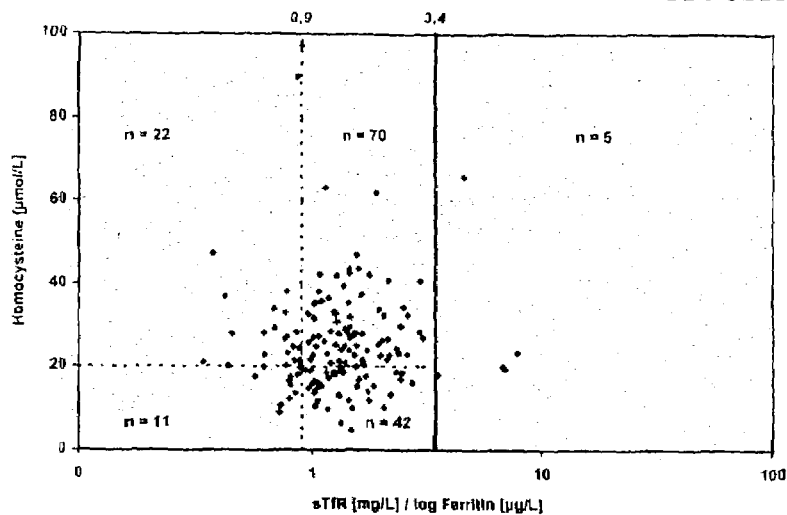
FIG. 12 shows that hyperhomocysteinemia is a risk factor in renal patients.
Figure 12B:
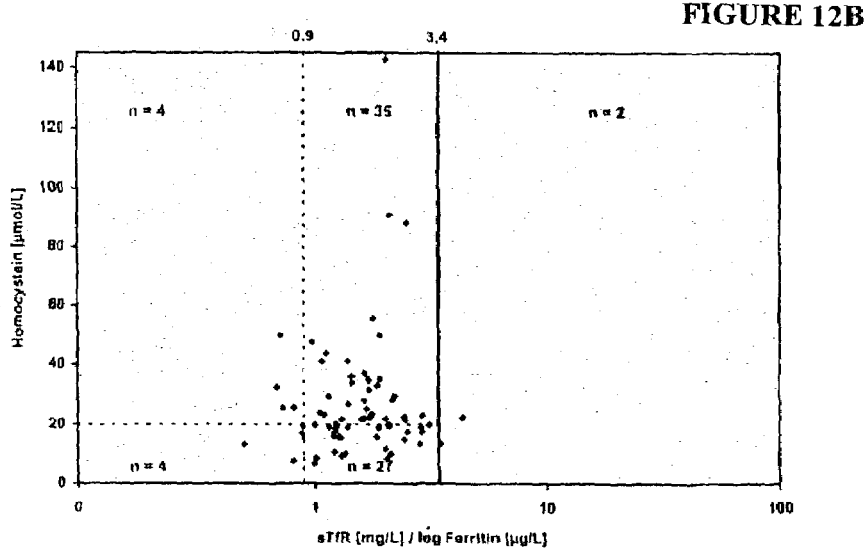
Figure 12C:
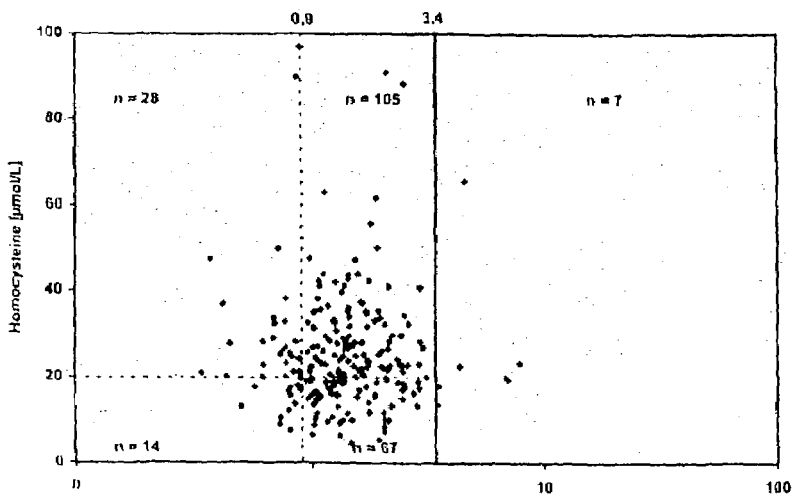

FIG. 11 shows the relationship between the CRP concentration and sTfR/log Ferritin in renal patients. FIG. 11a shows the results of study 1, FIG. 11b shows the results of study 2 and FIG. 11c shows the results of both studies in one graph. Field A indicates a likely disturbance of iron distribution, field B indicates an iron overload, field C indicates a normal iron status and field D indicates an iron deficiency.

This example shows that disorders of iron distribution can be described using Ferritin, the iron storage protein, and the soluble Transferrin Receptor, an indicator for cellular iron demand. Additionally erythropoietic activity can be estimated by determining the soluble Transferrin Receptor. CRP acts as an indicator of persistent acute phase reaction.

Homocysteine (HCY) is a marker of Hyperhomocysteinemia (HHCY). The high prevalence of HHCY in dialysis patients is caused by the disturbed renal remethylation of HCY and a functional Vitamin $B_{12}$, $B_6$ and Folate deficiency.

The determination of sTfR, Ferritin, CRP and Homocysteine in renal patients provides information about disturbances of erythropoietic activity (functional iron deficiency) and Hyperhomocysteinemia (HHCY). The data presume that the determination of these markers gives valuable information about a reduced ability to respond to Erythropoetin and i.v. Iron therapy influenced by Vitamin $B_{12}$, $B_6$ or Folate deficiency in renal patients. Our findings indicate an interaction between HHCY and disturbances of iron distribution (functional iron deficiency).

An diminished ability in dialysis patients to respond to erythropoietin and i.v. iron therapy can be caused by the disturbed renal remethylation of HCY and/or a functional Vitamin $B_{12}$, $B_6$ and Folate deficiency.

Example 6

Determination of sTfR, Ferritin and CRP as Markers in the Diagnosis of Anemias in a Reference Group of Adults Anemias are a worldwide problem. Severe anemias affect mainly elderly subjects. The most frequently-occurring iron metabolism anemias are iron deficiency and disturbances of iron distribution. They are hypochromic anemias and are often microcytic or normocytic. In addition to iron deficiency, which is widespread, disturbances of iron distribution caused by tumors, infections or chronic inflammations are increasing markedly.

TABLE 6

Classification of anemias based on hemoglobin, erythrocyte indices (MCH, MCV) and reticulocyte count

|  | microcytic | normocytic | macrocytic |
|---|---|---|---|
| Hb [g/dL] | M < 13.5 | M 14-17.5 | M > 18 |
|  | W < 12.5 | W 12.5-15.5 | W > 16 |
|  | Ch < 11.5 | Ch 11.5-15.5 | Ch > 16 |
| MCH [pg] | hypochromic | normochromic | hyperchromic |
|  | <28 pg/cell | 28-33 pg/cell | >33 pg/cell |
| MCV [fl] | microcytic | normocytic | macrocytic |
|  | <80 | 80-96 | >96 |
| Reticulocyte count [% of erythrocyte count] | hyporegenerative <5 | normoregenerative 5-15 | hyperregenerative >15 |

M = men, W = women, Ch = children
In addition to the hemoglobin value, the erythrocyte indices
MCH = Hemoglobin content of erythrocytes or the mean cellular hemoglobin
MCV = Mean cell volume of erythrocytes
are most important analytes.

Approximately 500 individuals were selected in age dependent groups (18-30; 30-40; 40-50 and 50->60 years). Each decade consisted of approximately 125 individuals and similar numbers of males and females. Participants were interviewed according to a questionnaire. Exclusion criteria were: Diabetes mellitus type I and II, Myopathies, burns and muscle traumas, Hypothyreosis, Chronic nephropathies and Chronic infection. Subjects suitable for inclusion were tested for the following parameters: HbA1c, ALT, GGT, CHE, Creatinine, fasting Glucose, CRP, Uric Acid, Triglycerides, Cholesterol, blood cell count and RBC/WBC indices (RBC, WBC, PLT, Hb, Hct, MCV, MCH, MCHC).

EDTA-samples from 482 healthy, non-diabetic adults were obtained from an institute for clinical pathology. Among these donors, 222 were males and 260 were females. Ages ranged from 18 to 70 years.

TABLE 7

Reference Population: Selection of Individuals

|  |  | Female | Male | All |
|---|---|---|---|---|
| Whole group: | 18-65 years | 260 | 214 | 474 |
| Decades: | 18-29 years | 66 | 59 | 125 |
|  | 30-39 years | 63 | 57 | 120 |
|  | 40-49 years | 67 | 47 | 114 |
|  | 50-59 years | 37 | 35 | 72 |
|  | ≧60 years | 27 | 16 | 43 |

Statistical Evaluation

TABLE 8

Statistical evaluation of Hb-, MCV-, MCH-values and Age- and Sex-Dependence

| | | Hb | | MCV | | MCH | |
|---|---|---|---|---|---|---|---|
| Group | n | median | max | median | max | median | max |
| Females | | | | | | | |
| all | 230 | 14.7 | 20.1 | 91 | 103 | 30.0 | 34.4 |
| 18-29 years | 57 | 14.9 | 17.3 | 91 | 101 | 29.7 | 33.2 |
| 30-39 years | 55 | 14.6 | 17.6 | 90 | 98 | 29.8 | 32.6 |
| 40-49 years | 57 | 14.4 | 17.0 | 91 | 102 | 30.1 | 33.3 |
| 50-59 years | 37 | 14.8 | 16.9 | 92 | 103 | 30.3 | 34.4 |
| ≧60 years | 24 | 14.9 | 20.1 | 93 | 99 | 30.5 | 33.1 |
| Males | | | | | | | |
| all | 212 | 16.4 | 18.8 | 90 | 99 | 30.2 | 32.8 |
| 18-29 years | 58 | 16.7 | 18.6 | 90 | 96 | 30.2 | 32.1 |
| 30-39 years | 56 | 16.3 | 18.1 | 90 | 98 | 30.1 | 32.8 |
| 40-49 years | 47 | 16.2 | 18.1 | 90 | 97 | 30.0 | 32.2 |
| 50-59 years | 35 | 16.3 | 18.8 | 91 | 99 | 30.4 | 32.7 |
| ≧60 years | 16 | 16.6 | 18.4 | 91 | 95 | 30.8 | 33.1 |
| Total Group | 442 | 15.4 | 20.1 | 91 | 103 | 30.1 | 34.4 |

TABLE 9

Statistical evaluation of CRP-, sTfR-, Ferritin-values and Age- and Sex-Dependence

| | | CRP [mg/L] | | sTfR [mg/L] | | Ferritin [μg/L] | |
|---|---|---|---|---|---|---|---|
| Group | n | median | max | median | max | median | max |
| Females | | | | | | | |
| all | 230 | 1.6 | 14.5 | 3.1 | 6.9 | 35 | 306 |
| 18-29 years | 57 | 1.8 | 14.5 | 3.1 | 5.3 | 30 | 108 |
| 30-39 years | 55 | 1.4 | 12.8 | 3.0 | 6.1 | 31 | 306 |
| 40-49 years | 57 | 1.3 | 8.4 | 3.4 | 6.9 | 33 | 191 |
| 50-59 years | 37 | 1.8 | 10.0 | 3.1 | 4.7 | 55 | 249 |
| ≧60 years | 24 | 1.7 | 12.9 | 3.0 | 5.0 | 71 | 205 |
| Males | | | | | | | |
| all | 212 | 1.1 | 14.0 | 3.1 | 6.8 | 102 | 594 |
| 18-29 years | 58 | 0.8 | 7.6 | 3.1 | 5.2 | 98 | 264 |
| 30-39 years | 56 | 1.0 | 12.3 | 3.0 | 4.9 | 102 | 412 |
| 40-49 years | 47 | 1.4 | 10.9 | 3.2 | 6.7 | 102 | 504 |
| 50-59 years | 35 | 1.6 | 9.7 | 3.2 | 6.8 | 106 | 388 |
| ≧60 years | 16 | 1.7 | 14.0 | 3.2 | 4.5 | 13 | 594 |
| Total Group | 442 | 1.4 | 14.5 | 3.1 | 6.9 | 63 | 594 |

An efficient method for differentiating between anemias is to calculate the quotient of sTfR/log Ferritin. CRP discriminates inflammatory from non-inflammatory processes. Following cut-off values are proposed by experts:

| | |
|---|---|
| sTfR for patients with iron deficiency (w, m): | 4.4 and 5 mg/L |
| Ferritin for patients with iron deficiency (w, m): | 15 and 30 µg/L |
| Ferritin for patients with iron overload (w, m): | 150 and 400 µg/L |
| CRP for patients with persistent acute phase reaction: | >5 mg/L |

Figure 13A:
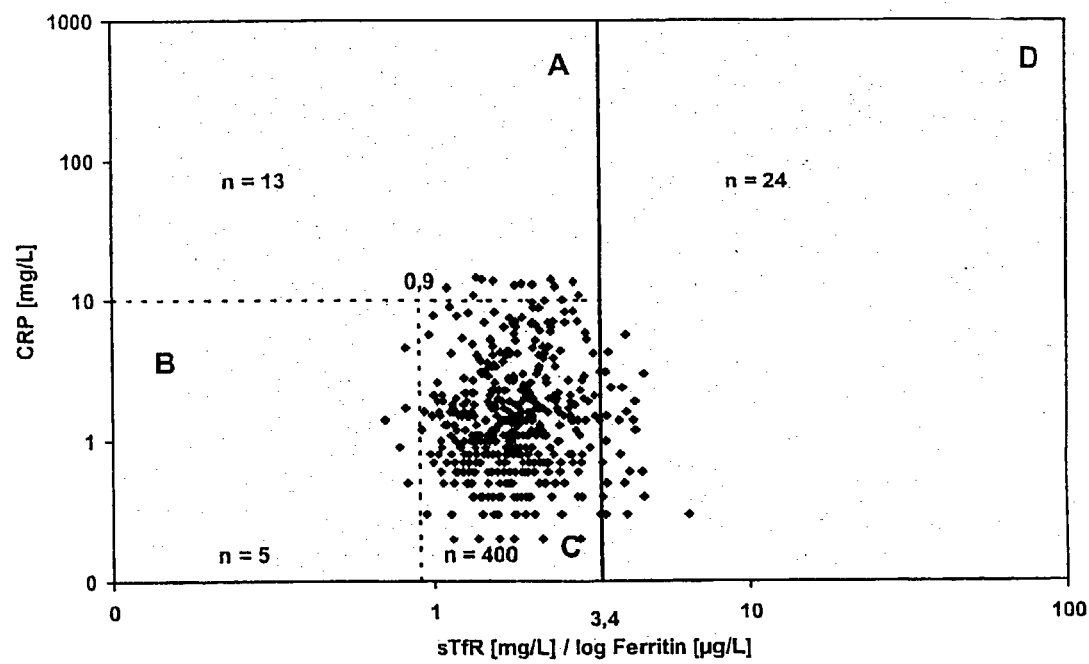
FIG. 13a shows the relationship between CRP concentration and sTfR/log ferritin in adults.
Figure 13B:
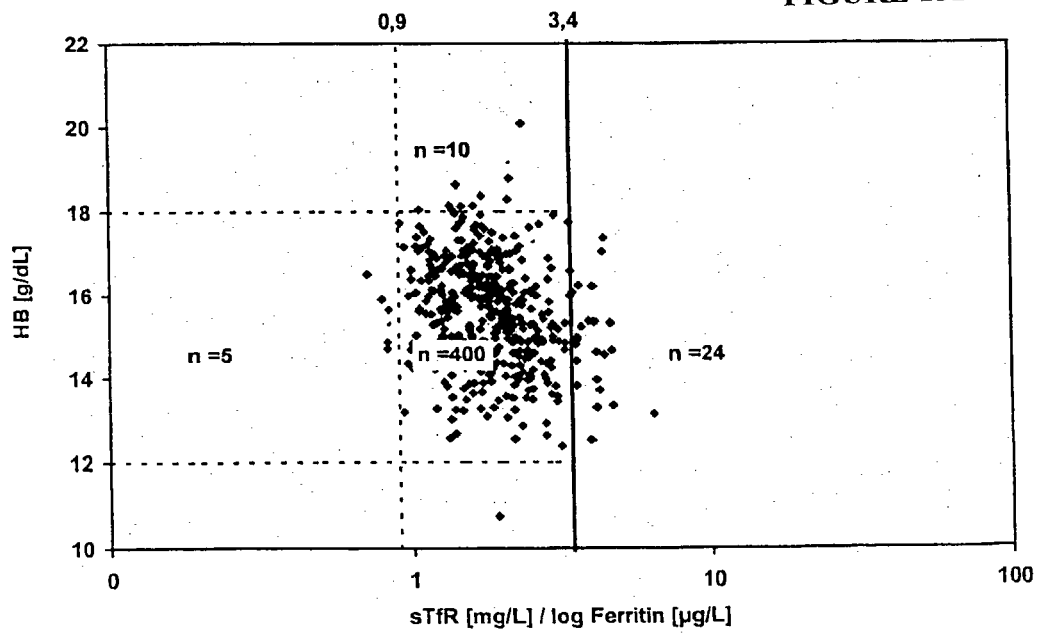
FIG. 13b shows the relationship between Hb and sTfR/log ferritin in adults.

FIG. 13a depicts the relationship between CRP concentration and sTfR/log Ferritin in adults (total group: n=442; female and male in the age of 18-70 years, cut-off CRP: 10 mg/L). Field A indicates a likely disturbance of iron distribution, field B indicates an iron overload, field C indicates a normal iron status and field D indicates an iron deficiency. FIG. 13b shows the relationship between Hb (g/dl) and sTfR/log Ferritin in adults (female and male in the age of 18-70).

Figure 14A:
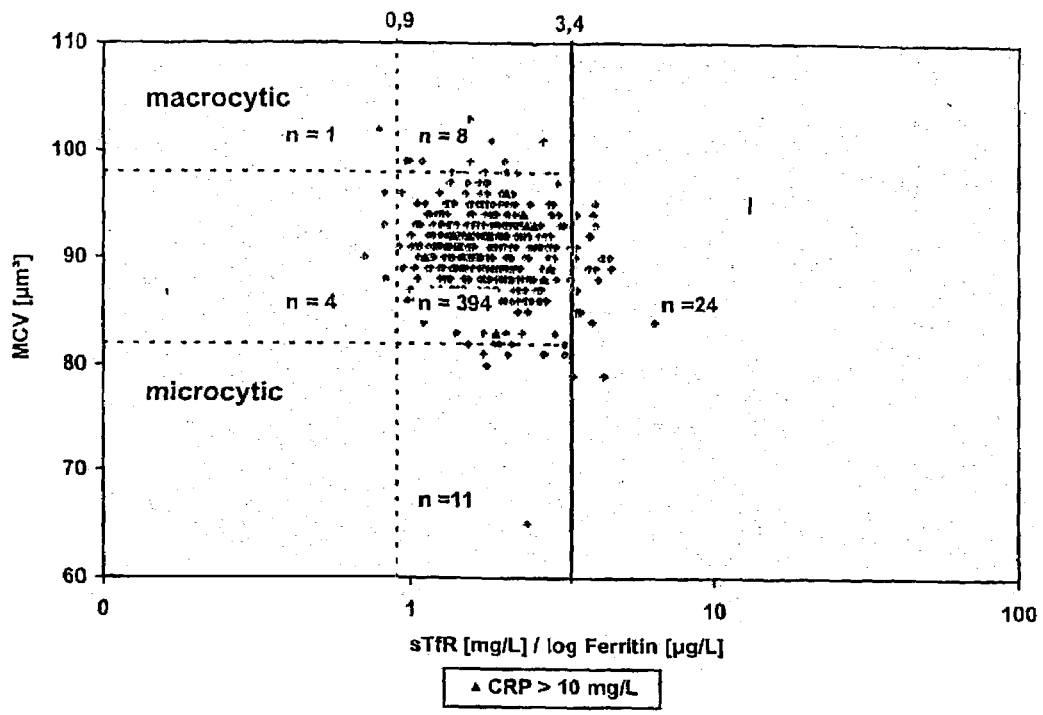
FIG. 14a shows the relationship between MCV and sTfR/log ferritin in adults.
Figure 14B:
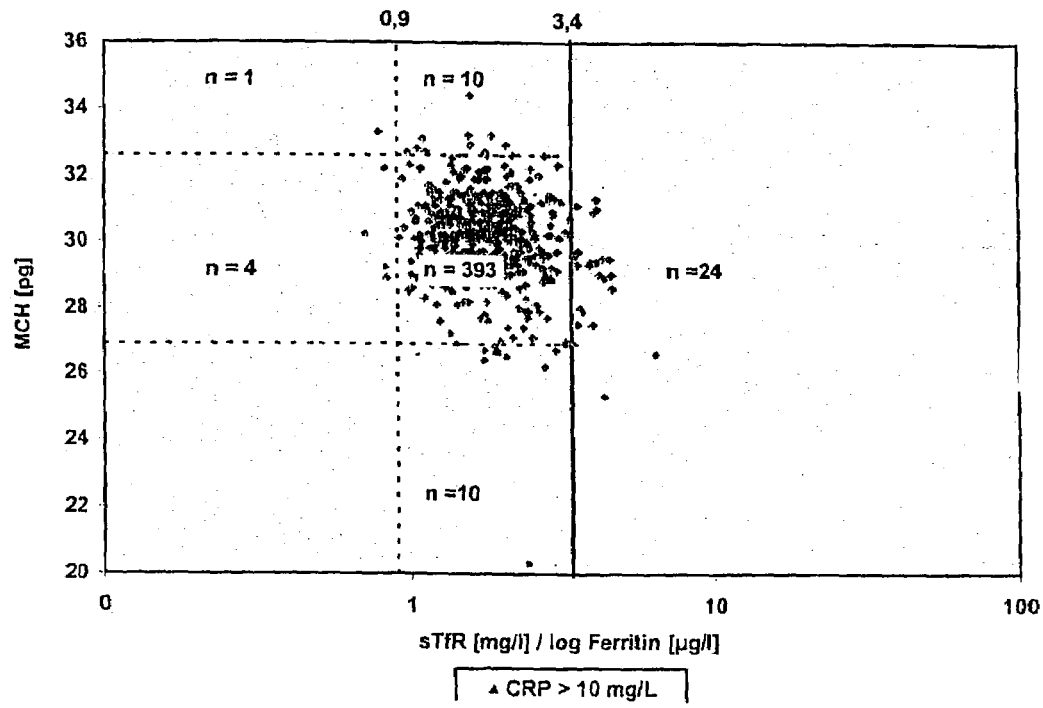
FIG. 14b shows the relationship between MCH and sTfR/log ferritin in adults.

In FIG. 14a the relationship between MCV and sTfR/log Ferritin in adults (female and male in the age of 18-70 years) is shown. FIG. 14b shows the relationship between MCH and sTfR/log Ferritin in adults (female and male in the age of 18-70 years).

This example shows that measurements of MCV, Ferritin, Soluble Transferrin Receptor and CRP are used in the diagnosis and monitoring of iron metabolism disorders.

This investigation summarizes the iron status of a healthy reference group of 442 adults.

A functional iron deficiency was found in 11 individuals. Elevated CRP-values (>10 mg/L) in 13 subjects and decreased MCV-values (<82 pg/cell) in 11 individuals suggested iron metabolism disorders accompanied by inflammatory processes. 22 females and 2 males suffered from manifest iron deficiency.

What is claimed is:

1. A method for identifying iron deficiency in a patient, the method comprising:
   (a) determining a level of each of the following in one or more samples from a patient:
      (i) ferritin,
      (ii) sTfR, and
      (iii) CHr;
   (b) plotting sTfR/log ferritin on a first axis of a plot and CHr on a second axis of the plot, the plot divided into quadrants, the quadrants defining specific iron deficiency classifications of:
      (1) no biochemical or haemotologically identified iron deficiency,
      (2) biochemically identified iron deficiency,
      (3) biochemical and haemotologically identified iron deficiency, and
      (4) haemotologically identified iron deficiency; and
   (c) determining the iron deficiency classification of the patient.

2. The method of claim 1 wherein the patient is classified as having (1) no biochemical or haemotologically identified iron deficiency or (2) biochemically identified iron deficiency when the level of CHr is equal to or greater than 28 pg/cell.

3. The method of claim 1, wherein the patient is classified as having (3) biochemical and haemotologically identified iron deficiency or (4) haemotologically identified iron deficiency when the level of CHr is less than 28 pg/cell.

* * * * *

UNITED STATES PATENT AND TRADEMARK OFFICE
CERTIFICATE OF CORRECTION

PATENT NO. : 7,659,074 B2
APPLICATION NO. : 10/449633
DATED : February 9, 2010
INVENTOR(S) : Roddiger et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 537 days.

Signed and Sealed this

Thirtieth Day of November, 2010

David J. Kappos
*Director of the United States Patent and Trademark Office*